US005789876A

United States Patent [19]
Umstadter et al.

[11] Patent Number: 5,789,876
[45] Date of Patent: Aug. 4, 1998

[54] METHOD AND APPARATUS FOR GENERATING AND ACCELERATING ULTRASHORT ELECTRON PULSES

[75] Inventors: Donald Umstadter; Joon-Koo Kim; Evan Dodd, all of Ann Arbor, Mich.

[73] Assignee: The Regents of the Univeristy of Michigan, Ann Arbor, Mich.

[21] Appl. No.: 528,078

[22] Filed: Sep. 14, 1995

[51] Int. Cl.$^6$ ................................................. H01J 23/00
[52] U.S. Cl. ........................ 315/507; 315/501; 315/505; 315/111.81
[58] Field of Search ........................ 315/507, 500, 315/505, 501, 111.81; 359/342; 378/119, 122

[56] References Cited

U.S. PATENT DOCUMENTS

| | | | |
|---|---|---|---|
| 4,655,547 | 4/1987 | Heritage et al. | 350/162.12 |
| 4,764,930 | 8/1988 | Bille et al. | 372/23 |
| 4,875,213 | 10/1989 | Lo | 372/5 |
| 4,910,746 | 3/1990 | Nicholson | 372/68 |
| 4,928,316 | 5/1990 | Heritage et al. | 455/600 |
| 4,937,532 | 6/1990 | Dawson et al. | 330/4.3 |
| 4,975,655 | 12/1990 | Dawson et al. | 330/4.3 |
| 5,003,543 | 3/1991 | Morsell et al. | 372/5 |
| 5,089,711 | 2/1992 | Morsell et al. | 250/492.3 |
| 5,151,928 | 9/1992 | Hirose | 378/119 |
| 5,175,757 | 12/1992 | Augustoni et al. | 378/120 |
| 5,235,606 | 8/1993 | Mourou et al. | 372/25 |
| 5,353,291 | 10/1994 | Sprangle et al. | 372/5 |

OTHER PUBLICATIONS

T. Tajima and J.M. Dawson, "An Electron Accelerator Using a Laser", IEEE Transactions on Nuclear Science, vol. NS–26, No. 3, Jun. 1979.

T. Tajima and J.M. Dawson, "Laser Electron Accelerator", Physical Review Letters, vol. 43, No. 4, Jul. 23, 1979.

T. Tajima and J.M. Dawson, "Laser Beat Accelerator", IEEE Transactions on Nuclear Science, vol. NS–28, No. 3, Jun. 1981.

L.M. Gorvunov and V.I. Kirsanov, "Excitation of Plasma Waves by an Electromagnetic Wave Packet, " Sov. Phys. JETP 66 (2), Aug. 1987.

P. Sprangle, E. Esarey, A. Ting, and G. Joyce, "Laser Wakefield Acceleration and Relativistic Optical Guiding, " Appl. Phys. Lett. 53 (22), Nov. 28, 1988.

S.V. Bulanov, V.I. Kirsanov, and A.S. Sakharov, "Excitation of Ultrarelativisitic Plasma Waves by Pulse of Electromagnetic Radiation", American Institute of Physics JETP Lett., vol. 50, No. 4, Aug. 25, 1989.

P. Sprangle, E. Esarey, and A. Ting, "Nonlinear Interaction of Intense Laser Pulses in Plasmas", Physical Review A, vol. 41, No. 8, Apr. 15, 1990.

J. Squier, F. Salin, and G. Mourou, "100–fs Pulse Generation and Amplification in Ti:A1203", Optics Letters, vol. 16, No. 6, 757–762, 1991.

V.I. Berzhiani and I.G. Murusidze, "Interaction of Highly Relativistic Short Laser Pulses with Plasmas and Nonlinear Wake–field Generation", Physica Scripta 45, 1991.

J. Squier and G. Mourou, "Tunable Solid–State Lasers Create Ultrashort Pulses", Laser Focus World, Jun. 1992.

(List continued on next page.)

*Primary Examiner*—Ashok Patel
*Attorney, Agent, or Firm*—Barnes, Kisselle, Raisch, Choate, Whittemore & Hulbert, P.C.

[57] ABSTRACT

The invention provides a novel laser-plasma-based source of relativistic electrons; and a method to use laser-driven plasma waves as the basis for the source of electrons. The technique involves a combination of laser beams, which are focused in a plasma. One beam creates a wakefield plasma wave. In one embodiment, the one beam creates a wakefield plasma wave and the other beam alters the trajectory of background electrons, such that they become trapped in the plasma wave and are then accelerated to relativistic velocities, preferably in a distance less than a millimeter. In another embodiment, the second beam removes electrons from atomic ions previously generated by the first beam thereby providing electrons which become trapped in the plasma wave and then accelerated to relativistic velocities.

48 Claims, 8 Drawing Sheets

OTHER PUBLICATIONS

D.H. Reitze, A.M. Weiner, and D.E. Leaird, "Shaping of Wide Bandwidth 20 Femtosecond Optical Pulses", Appl Phys. Lett. 61 (11), Sep. 14, 1992.

D. Umstadter, E. Esarey, and J. Kim, "Nonlinear Plasma Waves Resonantly Driven by Optimized Laser Pulse Trains", Physical Review Letters, vol. 72, No. 8, Feb. 21, 1994.

H.C. Kapteyn and M.M. Murnane, "Femtosecond Lasers: The Next Generation", Optics & Photonics News, Mar. 1994.

D. Umstadter, J. Workman, A. Maksimchuk, X. Liu, C.Y. Chien, and S. Coe, "Laser–Produced Picosecond Soft X–Ray Continuum Radiation", Proceedings of the International Conference on Lasers " 93, 165–170, Aug. 1994.

B.R. Marx, "Terawatt Lasers Generate X–Ray Continuum from Gold Target", Laser Focus World, 15–16, Feb. 1995.

D. Umstadter, J. Kim, E. Esarey, E. Dodd, and T. Neubert, "Resonantly Laser–Driven Plasma Waves for Electron Acceleration", Physical Review E, vol. 51, No. 4, Apr. 1995.

— VELOCITY
---- ELECTRIC FIELD
—·— ELECTRIC POTENTIAL

PHASE RELATIONSHIPS

ACTION OF PONDEROMOTIVE FORCE ON DEPHASING VELOCITY

FINAL DRIFT VELOCITY VS. LASER PULSE AMPLITUDE

METHOD AND APPARATUS FOR GENERATING AND ACCELERATING ULTRASHORT ELECTRON PULSES

GOVERNEMENT'S RIGHT CLAUSE

This invention was made with government support provided by the National Science Foundation. The government has certain rights in the invention.

FIELD OF THE INVENTION

This invention relates to a method and apparatus for accelerating particles in a plasma and more particularly to a method and apparatus of accelerating electrons to relativistic velocities.

BACKGROUND OF THE INVENTION

Since 1927, when Rutherford first proposed they be built, linear accelerators (linacs) have used either dc high-voltage or radio-frequency electric fields in vacuum to directly accelerate electrons from rest to MeV energies.

Current techniques for generating large amplitude plasma waves differ from each other essentially only in the temporal characteristics of the driving laser pulse(s), relative to the temporal characteristics of the plasma wave. For instance, the laser wakefield accelerator (LWFA) (FIG. 1) uses a single pulse with a pulsewidth $\tau \sim 2\pi/\omega_p$, where $\omega_p$ is the plasma frequency. The plasma beatwave accelerator (PBWA) (FIG. 2) uses a series of pulses of equal pulsewidths and equally spaced $\tau \sim 2\pi/\omega_p$. The self-modulated LWFA (SM-LWFA) and stimulated Raman forward scattering (SRFS), which are closely related, both use a single pulsewidth $\tau >> 2\pi/\omega_p$.

A plasma wave is an attractive acceleration medium because electrons can be accelerated to an energy of 3 GeV over a distance on the order of several meters. Besides applications in high-energy physics, the accelerated electrons can also be used to produce tunable short-wavelength radiation, either Bremstrahlung radiation from striking an anode as in an x-ray tube, or synchrotron radiation when they are passed through undulator magnets as in conventional synchrotron light sources of free-electron lasers, or when they collide (Compton scatter) with a laser pulse. Either the electrons themselves, or the high-energy photons into which they can be converted, have numerous industrial, medical and scientific applications, including: lithography, microscopy, spectroscopy, diffraction, metallurgy, radiology, oncology, and sterilization.

Conventional linacs produce an energy spread of accelerated electrons that is too great to be useful for most applications which require small electron-beam-energy spread. Conventional linacs are not able to produce a high-flux, small emittance, ultrashort-duration electron beam.

Accordingly, what is needed is a new method and apparatus to produce a high-flux, small-emittance, ultrashort electron beam.

SUMMARY OF THE INVENTION

The invention provides a novel laser-plasma-based source of relativistic electrons; and a method to use laser-driven plasma waves as the basis for the source of electrons. The technique involves a combination of laser beams, which are focused in a plasma. One beam creates a wakefield plasma wave.

In one embodiment, the one beam creates a wakefield plasma wave and the other beam alters the trajectory of background electrons, such that they become trapped in the plasma wave and are then accelerated to relativistic velocities, preferably in a distance less than a millimeter. In another embodiment, the second beam removes electrons from atomic ions previously generated by the first beam thereby providing electrons which become trapped in the plasma wave and then accelerated to relativistic velocities in the aforesaid short distance. For simplicity, the first beam is referred to as the pump pulse and the second beam is referred to as the injection pulse. In one aspect of the invention, acceleration of electrons is made possible by dephasing the electrons with respect to the plasma wave by using ponderomotive force. In another aspect, the dephased electrons are also created essentially instantaneously at a given point in the plasma wave by the injection pulse which removes electrons from atomic species in the plasma at a higher ionization stage than that of the electrons previously removed by ionization by the pump pulse which forms the plasma wave. Combinations of various numbers of pulses at varying intensities, pulse time duration (pulsewidth), wavelength, and polarization are used to achieve the dephased electrons for acceleration.

In one embodiment, a single pump pulse and a single injection pulse are used where the pump and injection beams are orthogonal to one another. In another embodiment, two injection pulses are used which are delivered in a beam in a direction orthogonal to the pump pulse beam. The two injection beams are counter-propagating, that is, opposite to one another. In still another embodiment, the pump pulse is followed by an injection pulse which is collinear with the pump pulse but is at a higher intensity.

In still another embodiment, first and second pump pulses are used along with an injection pulse. The second pump pulse is generated at an interval of 3/2 plasma wavelengths $(3/2\lambda_p)$ after the first pump pulse, to provide an acceleration region of a single plasma wavelength and thus provide a single accelerated electron bunch.

In still another embodiment, the pump pulse causes the plasma wave which has an axial dimension (z axis) and a radial dimension (y axis); and the injection pulse is focused onto the plasma wave by focusing means which provides a beam spot size having a dimension along the y axis which is greater than the size along the z axis. Preferably, the injection pulse is focused onto the plasma wave by focusing means which provides a beam spot size, which in one dimension substantially corresponds to the radial extent of the plasma wave, and in another dimension corresponds to about one plasma wave wavelength $(\lambda_p)$. The method of the invention locally disturbs the plasma wave and generates a group of electrons that are dephased with respect to the plasma wave and thereby come under the influence of the electric field of the plasma wave permitting such electrons to be accelerated. As a result, the invention provides both the source of accelerated electrons as well as the means for their acceleration. This avoids cumbersome conventional apparatus and methods which require separate expensive systems for generating electrons, i.e., electron guns, and for accelerating electrons, i.e., linear acceleration (linac).

In still another embodiment, two pump pulses are used. A first pump pulse generates the plasma and the second pump pulse creates the plasma wave. The first pump pulse ionizes the plasma to high ionization stage and the second pump pulse, delayed by greater than several ion periods creates a plasma wave after the plasma wave from the first pump pulse has damped away, but not after plasma recombination. A third pulse which is the injection pulse ionizes the plasma one stage further and injects electrons with high velocity.

The maximum residual velocity of the electrons depends on the intensity at which such electrons were created by ionization. In this embodiment, desirably the pump pulse and the injection pulse have differing polarizations. In this embodiment, the injection pulse is preferably circularly polarized and the other pulses, pump pulses, are linearly polarized. Other combinations besides linear and circular polarization are also possible, namely, elliptical polarization variations. This approach decouples the plasma wave generation from the ionization, thus avoiding a change in plasma density during the second pump pulse.

In the method of the invention, if it is desired to accelerate electrons by changing trajectory via ponderomotive force only, it is preferable to use hydrogen, which has one electron. If it is desired to generate a group of dephased electrons by removing electrons from atomic ions in the plasma, then it is preferable to use a higher order atom, such as, for example, argon.

It should be noted that the disturbance necessary to generate the dephased electrons does not totally destroy the plasma wave. The disturbance is localized in the direction of the pump pulse. In the case of a transverse injection beam, it propagates in a direction which does not disturb the rest of the plasma wave momentarily since the disturbance by ponderomotive force propagates in the direction of the pump pulse at a much slower speed compared to the phase velocity of the plasma wave. If a wake is created by the transverse injection beam moving along a y axis perpendicular to a z axis, it does not propagate in the direction of the pump pulse (along z axis) at nearly the same velocity as either the wake of the pump pulse or the trapped electrons. Therefore, when the injection pulse arrives it pushes electrons radially (in the z direction in the plane of the y axis) so as to dephase their normal orbits. This disturbance does propagate in the z direction which is the direction of the pump pulse. However, the velocity at which the wave is moving is much higher than the velocity at which the disturbance moves. As a result, it is possible to dephase a group of electrons, accelerate them, and achieve a final accelerated bunch of electrons which are essentially mono-energetic, where all of the electrons have essentially the same energy, or very close to the same energy, for example, plus or minus 10 percent. The pulse width of the accelerated electrons is ultrashort and approaches the pulsewidth of the laser that generated them and may even be shorter.

Importantly, the pulses of the invention are ultrashort pulses generated by a specific configuration of a laser system as described herein. In the method of the invention, the pump pulse and the injection pulse may be obtained from the same laser beam by splitting a single laser pulse into two sub-pulses, one of which is used as the injection pulse and the other of which is used as the pump pulse. The beamsplitting may occur before or after recompression in the laser system. If such beamsplitting occurs after recompression, then the pump and injection pulses are synchronized with respect to one another. Such synchronization is very difficult to achieve by conventional systems which require independent devices, one being an electron generator and the other being the laser to produce a plasma wave. The invention may also be used with the beamsplitter prior to recompression, in order to achieve pump pulse and injection pulse of different pulse time durations.

The invention advantageously utilizes laser-driven plasma waves as the first-stage low-energy electron gun/linac itself. As such, it forms the basis for a compact (table-top) source of relativistic electrons, that can either be used by itself or as an injector for high-energy accelerators.

Electrons are accelerated to relativistic velocities in a distance less than a millimeter, as compared with several meters for a comparable conventional linac. This results in lower beam emittance and a more compact size. It also produces much shorter-duration electron pulses (femtosecond as compared with picosecond). For applications that require an electron bunch synchronized with a laser-light pulse, femtosecond accuracy may be achieved with the invention. Two orthogonally directed laser beams are injected into a plasma: one beam creates a wakefield plasma wave, and the other alters the trajectory of background electrons in such a way that they become trapped in the plasma wave and are then accelerated to relativistic velocities in a distance less than a millimeter. As the technique involves the injection of electrons by a laser beam, it is referred to as the Laser-Injected Laser ACcelerator (LILAC). Compared with a conventional electron linac, the LILAC has a much higher field gradient, resulting in lower beam emittance. Since it also can produce much shorter-duration electron pulses, it can be used for the study of ultrafast dynamics on femtosecond timescales. The invention also enables femtosecond-synchronization between the electron bunch and the plasma wave acceleration field, which is required to achieve a low-energy spread for the accelerated electrons. A high-flux low-emittance beam of 20-MeV electrons can be produced with a currently-available table-top high-intensity laser ($I \leq 1 \times 10^{18}$ W/cm$^2$). The principle upon which the LILAC is based can be used to study the growth of, and the trapping of electrons in, laser wakefield plasma waves.

Advantageously, the invention (LILAC) provides an improved method and apparatus to accelerate electrons. It is capable of accelerating electrons from rest to energies ranging anywhere from an MeV to greater than a GeV (with optical guiding). The invention (LILAC) can produce a high-flux, small-emittance, ultrashort-duration (subpicosecond) electron beam. For applications requiring a single ultrashort bunch of electrons, such as ultrafast dynamical studies, a single bucket can be generated. This novel electron gun could serve several purposes: (1) as a stand-alone accelerator system, (2) as a low emittance injection stage for conventional accelerators, or (3) as a means to study the physics of laser-wakefield plasma waves. Accordingly, femtosecond synchronization between the electron bunch and a single-plasma-wave-acceleration bucket is made possible for the first time by the invention.

Advantageously, the invention provides, high flux, small emittance (beam energy spread) and ultrashort duration (subpicosecond) electron beam.

Accordingly it is a general object of the invention to provide a method and apparatus for producing electrons accelerated to relativistic velocities.

Another object is to provide a method and apparatus for creating dephased electrons, dephased with respect to a plasma wave for acceleration of said electrons via plasma wave electric field.

Another object is to provide a combination of laser pulses having a combination of characteristics and direction with respect to one another where one beam creates a wakefield plasma wave and the other beam alters the trajectory of background electrons for trapping by the plasma wave and acceleration to relativistic velocities.

Still another object is to provide a combination of laser beams which form a plasma, form a plasma wave in the plasma, and inject electrons for acceleration to relativistic velocities, without the need for a separate conventional electron source.

Still another object is to provide femtosecond duration electron pulses produced by a combination of laser beams.

Still another object is to provide electrons accelerated to relativistic velocities in a distance less than a meter, and in as little as a millimeter or less.

These and other objects, features, and advantages of the invention will become apparent from the following description of the preferred embodiments, claims, and accompanying drawings.

DETAILED DESCRIPTION OF THE PREFERRED EMBODIMENTS

Before describing the invention in detail, it is useful to understand the problems associated with present acceleration methods.

Current laser-driven plasma waves have been used, or proposed to be used, exclusively for second-stage high-energy electron acceleration of a trailing bunch of electrons. In this case, prior to injection into the plasma wave, the trailing bunch of electrons must first be generated and pre-accelerated ($\gamma mc^2 \leq 5$ MeV) by means of a conventional electron gun/accelerator, such as a medical linac (radio-frequency) or Van de Graaff generator (dc).

Figure 1:
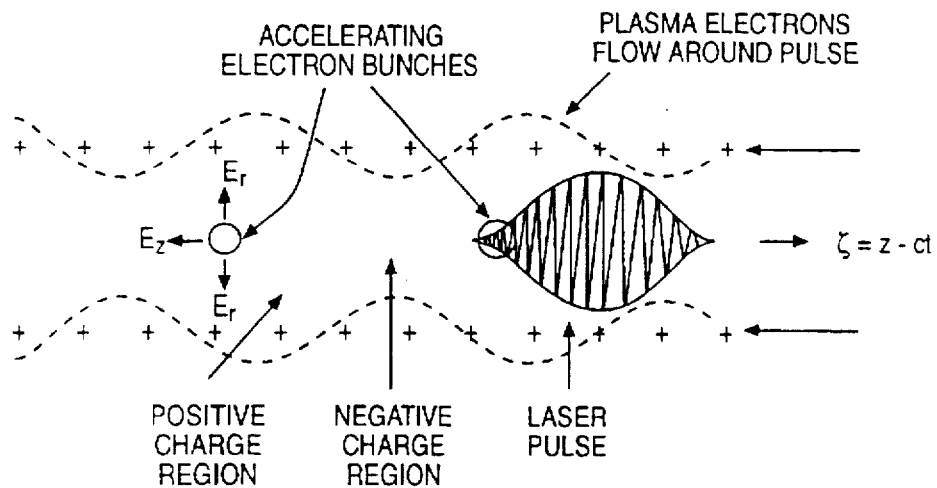
FIG. 1 is a schematic of a laser wakefield accelerator (LWFA) showing the ponderomotive force from a laser pulse generating a plasma wave wake in a plasma.
Figure 2:
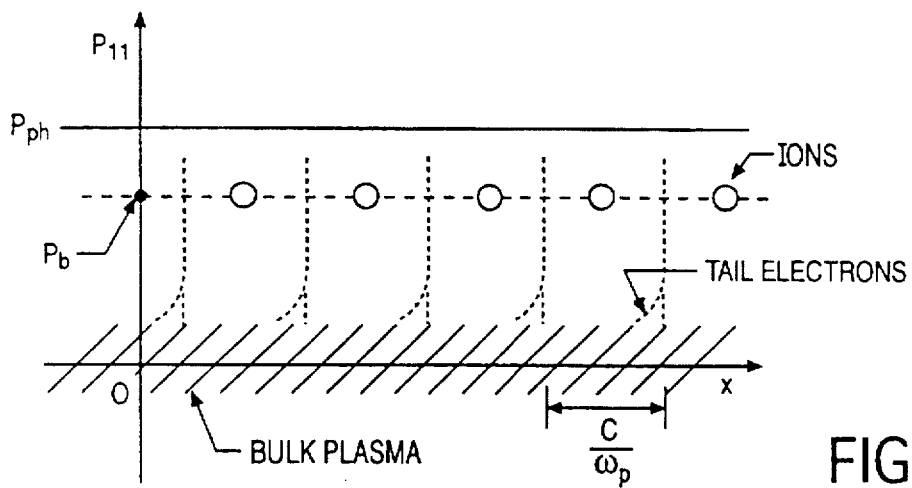
FIG. 2 is a schematic phase space diagram showing bulk electrons, tail electrons, and pre-accelerated ions where $P_{ph}$ represents the phase momentum of the plasma wave excited by laser and $P_b$ is the ion beam momentum, ion clump separation is designated as $c/\omega_p$.

Current techniques for generating large amplitude plasma waves differ from each other essentially only in the temporal characteristics of the driving laser pulse(s), relative to the temporal characteristics of the plasma wave. For instance, the laser wakefield accelerator (LWFA) (FIG. 1) uses a single pulse with a pulsewidth $\tau \sim \pi/\omega_p$, where $\omega_p$ is the plasma frequency. The plasma beatwave accelerator (PBWA) (FIG. 2) uses a series of pulses of equal pulsewidths and equally spaced $\tau \sim \pi/\omega_p$. The self-modulated LWFA (SM-LWFA) and stimulated Raman forward scattering (SRFS), which are closely related, both use a single pulse with $\tau >> 2\pi/\omega_p$.

All of these current techniques for accelerating electrons with a plasma wave involve the acceleration of a trailing bunch of properly-phased electrons. The injection threshold (the energy at which the electrons become trapped by the wave) depends on both the plasma-wave amplitude and phase velocity, obtained by setting the plasma wave potential equal to the electron's kinetic energy (in the wave frame). In order to be trapped by, and thus gain energy from, a plasma wave, the electrons must already have significant kinetic energy. The lower the plasma wave amplitude, and the higher the value of $\gamma_p$, the higher the kinetic energy required, where $\gamma_p = (1 - v_p^2/c^2)^{-1/2}$, and $v_p$ is the plasma-wave phase velocity. Background plasma wave electrons, which oscillate in-phase with each other, will not be accelerated until the plasma wave reaches the wavebreaking amplitude, $E_{WB} = E_0 \sqrt{2(\gamma_p - 1)}$, where $E_0 = (m_e c \omega_p / e) \approx 0.96 n_0^{1/2} [cm^{-3}] V/cm$. Even if the plasma wave breaks, the energy spread of any electrons that are accelerated in this way will be too large to be useful for most applications, which require small electron-beam-energy spread.

For this reason, conventional low-energy electron linacs (such as those that use microwave cavities) are used to first accelerate a trailing bunch of electrons from rest up to the required injection energies. Typically, these have low-field gradients (6.5 MeV/m), and, for a short-pulse synchronized electron bunch, have a laser-triggered photocathode for the electron source. Coupling the electron bunch generated by this linac to a laser-plasma accelerator is quite difficult and complicated, requiring precise temporal and spatial overlap with micron accuracy. Even with state-of-the-art electrons guns, the pulsewidth of the electron bunch is considerably longer ($\tau \geq 5$ ps) than a plasma wave period ($\tau \leq 1$ ps). For this reason, multiple acceleration buckets are filled uniformly in-phase space, resulting in a large-energy spread of the accelerated electrons and several bunches. More than a single bunch per pulse would make ultrafast studies difficult. Also, in a conventional electron gun/high-energy accelerator system, the largest electron-emittance growth occurs due to dispersion over the long-acceleration lengths of the low-energy first-stage conventional electron linac.

Figure 3:
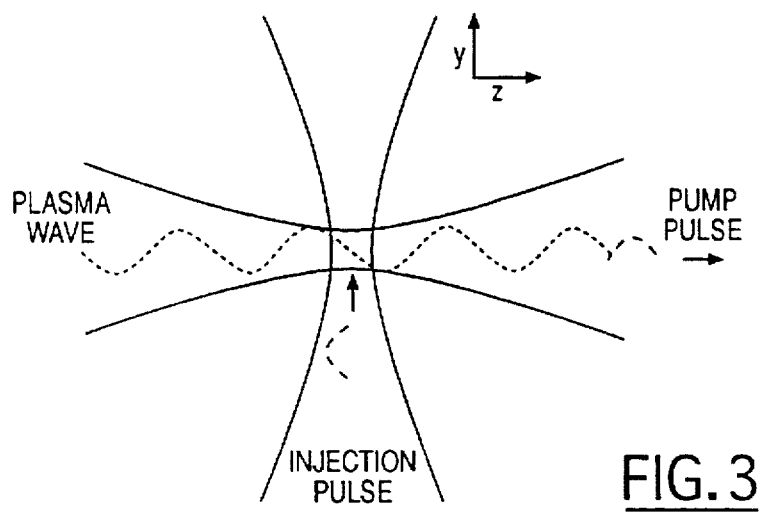
FIG. 3 shows a schematic of the laser injected laser accelerator concept of the invention.

The invention provides a new method and apparatus for obtaining relativistic electrons. This system is unlike other plasma-based accelerators, which are exclusively second stage electronic accelerators requiring a trailing bunch of electrons that have been generated and pre-accelerated in a conventional combination electron gun and linear accelerator. The invention provides a method and apparatus to use laser driven plasma wave in place of the less effective conventional electron gun/linear accelerator. The method involves a combination of laser pulses focused in a plasma in a particular manner, as shown in FIG. 3.

In the description of the invention, the following terms are used: (1) ion period is the time it takes for ions to have a single cycle in plasma oscillation; (2) recombination is the reverse process of ionization of neutral atoms; (3) damped away refers to the plasma wave amplitude, either can increase or decrease by the wave particle interaction called Landau damping; (4) residual velocity refers to the situation when laser intensity reaches Above Threshold Ionization (ATI) intensity, plasma electrons are born from neutral atoms with certain velocity, this is called residual velocity; (5) trapped refers to the situation if the kinetic energy of a particle is less than the potential energy of the wave in the reference frame of the wave, then the particle is said to be trapped in the wave; and (6) drift velocity is analogous to residual velocity and refers to velocity imparted by ponderomotive force.

The invention provides a novel laser-plasma-based source of relativistic electrons; and a method to use laser-driven plasma waves as the basis for the source of electrons. The technique involves a combination of laser beams, which are focused in a plasma. One beam creates a wakefield plasma wave. In one embodiment, another beam (injection pulse) alters the trajectory of background electrons, such that they become trapped in the plasma wave and are then accelerated to relativistic velocities in a distance preferably less than a millimeter.

The wakefield plasma wave of the invention is driven by a pump beam. In one embodiment, a pump beam of a single pulse is used as the laser wakefield accelerator. The pump beam and the wakefield plasma wave are co-propagating. The other beam (the injection beam) is used to trap electrons in the plasma wave wakefield. A variably-delayed injection pulse, propagating in the direction perpendicular to the propagation direction of a wakefield plasma wave, is brought to a focus on the plasma wave, preferably at an optimum point in space and time. It changes the trajectories of background electrons (oscillating in the plasma wave) such that they become trapped and accelerated by the plasma wave. In this embodiment, it is the ponderomotive force due to the transverse field gradient of the injection pulse that gives rise to the change in-phase and trapping of background electrons.

The injection pulse also has a longitudinal ponderomotive force, which can have deleterious effects: it can either (1) accelerate electrons in a direction orthogonal to that of the pump's wakefield or (2) create its own wake. In order to mitigate these effects, two counterpropagating injection beams are used to create longitudinal ponderomotive forces that cancel each other at the intersection point (a standing wave). This alternative may be preferred for some applications, but is not thought strictly necessary. The reasons are as follows. In the case of (1), even if electrons are given an initial kick in the direction orthogonal to the pump's wake, it will be quite small compared with the acceleration they feel once trapped by the wakefield. Since they all get the same kick, once they are accelerated to their final energy, they will all leave with the same small angle relative to the direction of the pump beam. So long as the electrons do not move in the transverse direction a distance more than a plasma wave radius, this initial kick should not be a problem, since it is only angular spread that increases electron-beam emittance. In the case of (2), even if a disturbance is created in the direction of the pump pulse by the transverse beam, it does not propagate in the direction of the pump at nearly the same velocity as either the wake of the pump or the trapped electrons. Thus, shortly after being injected, the trapped electrons will find themselves in an undisturbed region of the wave created by the pump. If necessary, the disturbance can be eliminated altogether if the transverse beam's pulse duration is adjusted so that it is wakeless, i.e., out of resonance with the plasma.

In another embodiment, the invention provides independent adjustment of the pulse duration of the injection pulse. Under certain circumstances, this could result in the injection of pulses into several buckets, for example, if it is longer than a plasma wave period, or the width of the plasma wave is greater than a plasma wavelength. Thus, if acceleration of just a single bunch of electrons is desired, only a single acceleration bucket must be created. This is accomplished by use of two pump pulses. The first pulse can be used to drive up the plasma wave, and the second, by arriving one and a half plasma periods later, can be used to drive it back down. Conversely, if it is desirable to fill several buckets, then this may be accomplished by use of either a long injection pulse or a train of injection pulses.

The method of accelerating electrons that are out of phase with a plasma wave is quite general. There are alternative embodiments, besides the use of the ponderomotive force of an injection pulse. For instance the injection pulse is used to create the out-of-phase (dephased) electrons by multiphoton, or tunneling, photo-ionization. In this case, a gas comprising an atom with several electrons is used. The pump pulse at its peak intensity ionizes the gas to a given ionization stage, then the injection pulse ionizes the gas further to a higher ionization stage, creating electrons that are out of phase with the plasma wave. These electrons are then accelerated in a manner similar to that discussed above.

If the ionization occurs at sufficiently high intensity, the electrons can be born (created) with a high enough residual velocity to become trapped in the plasma wakefield. In the case of circularly polarized light, the residual (drift) velocity is equal to the quiver velocity and is in a direction perpendicular to the direction of the laser electric field at the time when it was born. In the case of linearly polarized light, the residual energy is significantly less, equal to a fraction of the ponderomotive potential energy, and the drift velocity is along the direction of the laser electric field. Since the electric field vector rotates in the case of circularly polarized light, only a small fraction of the electrons created by ionization would be in the right direction to be injected, and the angular spread of the injected electrons would be higher, in comparison with the case of linear polarization.

A given ionization stage has a threshold that is proportional to both the laser intensity and the laser wavelength— the shorter the wavelength, the lower the intensity required for ionization. Accordingly, if the injection pulse is shorter wavelength than the pump, it can reach the required higher ionization stage with an intensity that is the same as, or even lower than, that of the pump. The use of circularly polarized light for the injection pulse increases the residual velocity of the ionized electrons for a given laser intensity, as compared with a linearly polarized pulse. Thus, the use of either short wavelength or circularly polarized light reduces the deleterious effect of the ponderomotive force of the injection pulse on the plasma wakefield.

In one embodiment, the injection pulse is orthogonal to the pump pulse. In another embodiment, the injection pulse is collinear with the pump pulse, considerably simplifying the alignment of the two pulses. In this regard, the laser pulses are generated by a resonant laser-plasma accelerator (RLPA). The RLPA uses a series of pulses with increasing spacing between them and decreasing pulsewidths to compensate for the change in resonance as the plasma wave grows and $\omega_p$ changes. In the collinear case, not only does the second pulse create dephased electrons, it is used to enhance the wake of the pump pulse. Circularly polarized pulses are preferably used in order to create the electrons with a high initial forward velocity and thus increase the number of trapped electrons. In the collinear case, the second pump pulse achieves two objectives. It creates dephased electrons and also enhances the wake of the first pump pulse. Circularly polarized pulses are preferably used in order to create the electrons with a high enough initial forward velocity to be trapped. However, in order to produce high axial electric fields, short focal lengths are required, which, without some method for channeling the beams, would reduce the acceleration length.

The basic system used for the laser-plasma interaction, preferably includes a plasma region that is located at the center of a vacuum chamber. A vacuum is necessary in order to avoid degradation of the high-intensity laser beam due to self-phase modulation. The electrons are coupled out of the vacuum through a thin-film-metal window. The plasma is created either by laser photo-ionization of a gas or by other means. The pump and injection beams are preferably generated by the same chirped-pulse-amplification laser by use of a beamsplitter, which is placed either before or after the final laser compressor. In the former case, the pulsewidths of the injection beam and pump beam could be made to be different from each other by using different compression ratios. Preferably, a cylindrical lens is used in the path of the injector pulse to tightly focus the injection beam in one dimension (along z axis) and loosely along the perpendicular to the plane of incidence formed by the two beams (x). The injection beam's dimension along this later (x) direction could be made to match that of the pump beam spotsize. The injection beam's intensity gradient would thus be large along z but not x, which minimizes the emittance of the accelerated electron beam. The pump beam is preferably loosely focused with a circular lens such that the plasma wave is as one dimensional (1-D) as possible. Information on the accelerated electron energy spectrum is preferably monitored with a magnetic spectrometer and fed back to the laser-delay system in order to optimize the electron beam parameters.

Electrons accelerated by the method of the invention, achieve an energy exceeding 10 MeV in a distance less than a millimeter, as compared to several meters in the case of conventional photocathode electron guns. This reduction in length results in a large reduction in the emittance growth, and thus increases the final-focus luminosity. By eliminating the need for a separate conventional injector, this technique also significantly reduces the complexity of electron accelerators. This is because it is considerably easier to temporally and spatially overlap two laser beams than a laser beam and an electron beam. Femtosecond synchronization between the electron bunch and a single-plasma-wave-acceleration bucket is now made possible with this technique. In another embodiment, the invention is used to study the physics of electron acceleration by wakefield plasma waves. In this embodiment, the delay between pump and injection pulses is varied and then the trapped electron energy gain is monitored to obtain detailed information on both the plasma wave amplitude (as a function of space or time) and the conditions required for trapping. In still another embodiment, a second injection laser pulse counterpropagating to the pump pulse is used to Compton scatter from the accelerated electron beam in order to create high-energy ($4\gamma^2$ hv) photons. This forms the basis for a compact source of ultrashort 10-KeV x-rays.

System Description

Figure 4:
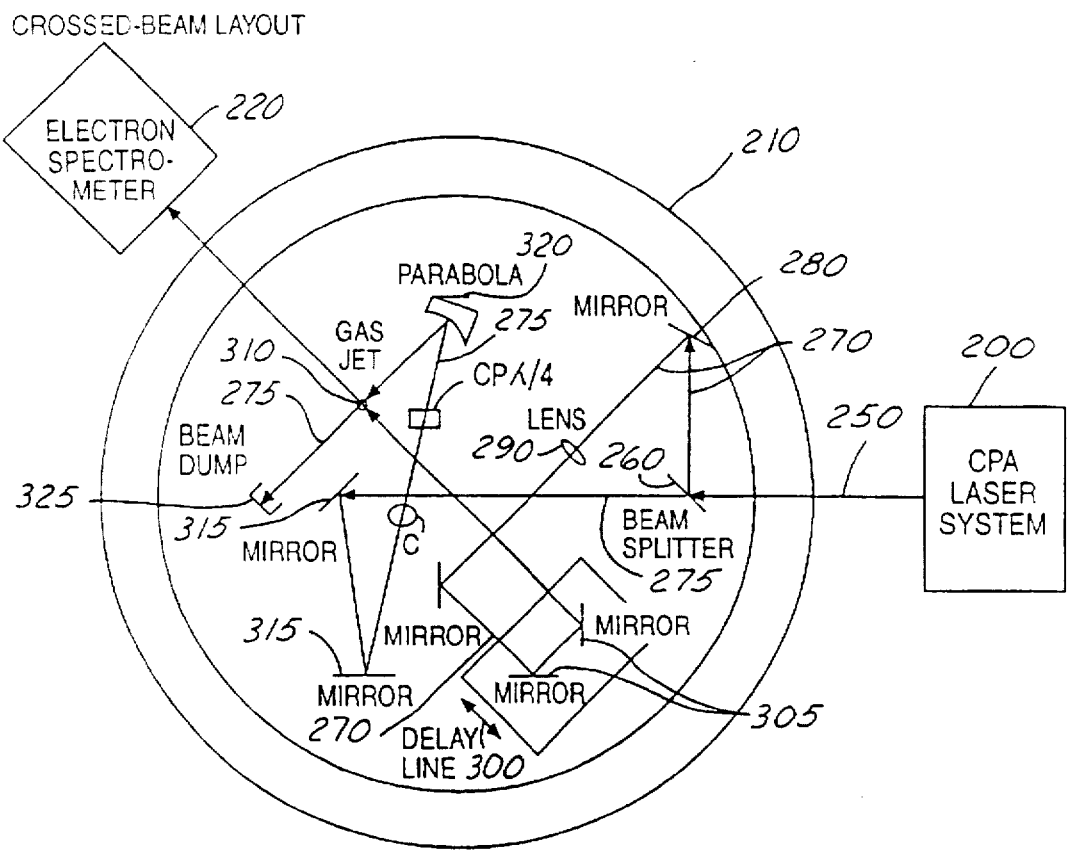
FIGS. 4 and 17 are schematic diagrams of the laser injected laser accelerator (LILAC) experimental systems of the invention.

An example of an experimental set-up for the laser-injector laser accelerator of the invention is shown in FIG. 4. The major components of the system are laser apparatus (200), vacuum target chamber (210), and electron spectrometer (220). Laser system (200) is preferably a chirped pulse amplification system, CPA system (200). The basic configuration of a CPA system used in the invention will be described more particularly below. The beam of laser light (250) generated from CPA laser (200) is split by beamsplitter mirror (260) into a first pulse (270) which is also referred to as a pump pulse and a second pulse (275) which is referred to as an injection pulse. Pump pulse (270) is directed by mirror (280) through focusing lens (290), preferably, a circular lens. Next, pump pulse (270) is directed to a delay line (300) which is composed of a number of reflective surfaces (305) and then directed onto target (310). Target (310) is any material. Preferably it is a gas, supplied as a jet of gas. As shown in FIG. 4, injection pulse (275) is directed by mirrors (315) onto parabolic lens (320). Lens (320) is preferably a cylindrical lens. Other lenses, such as spherical, may also be used. In the case of a cylindrical lens, the pump pulse (270) causes the plasma wave which has an axial extent (z dimension) and a radial extent (y dimension) and the injection pulse is focused onto the plasma wave by focusing means which provides a beam spot size having a dimension along the y axis which is greater than the size along the z axis. Preferably, the injection pulse is focused onto the plasma wave by focusing means which provides a beam spot size, which in one dimension substantially corresponds to the radial extent of the plasma wave, and in another dimension corresponds to about one plasma wave wavelength ($\lambda_p$). Injection pulse (275) is then disposed into beam dump (325). It is desirable to have pump pulse (270) arrive at target (310) first. Injection pulse (275) may arrive at target (310) during the time of pump pulse (270). Preferably, the two pulses (270), (275) are offset with respect to one another, the pump pulse (270) being ahead of the injection pulse (275). In short, the injection pulse (275) is delayed with respect to the pump pulse (270). If desired, the wavelength of the injection and/or pump pulse may be altered by passing through a frequency doubling or tripling crystal (2θ, 3θ) or by optical parametric amplification. The crystal (C) and the λ/4 wave plate circular polarizer (CP) are respectively shown in FIG. 4.

In the method of the invention, laser pulses are used having laser pulse width in the nanosecond to femtosecond range using a chirped pulse amplification (CPA) laser system. The basic configuration of such a CPA system is described in U.S. Pat. No. 5,235,606. U.S. Pat. No. 5,235,606 is incorporated herein by reference in its entirety.

Chirped pulse amplification systems can be roughly divided into four categories. The first includes the high energy low repetition systems such as ND:glass lasers with outputs of several joules but they may fire less than 1 shot per minute. A second category are lasers that have an output of approximately 1 joule and repetition rates from 1 to 20 hertz. The third group consists of millijoule level lasers that operate at rates ranging from 1 to 10 kilohertz. A fourth group of lasers operates at 250 to 350 kilohertz and produces a 1 to 2 microjoules per pulse. In U.S. Pat. No. 5,235,606 several solid state amplifying materials are identified and the invention of U.S. Pat. No. 5,235,606 is illustrated using the Alexandrite. Ti:Sapphire is also commonly used in the basic process of U.S. Pat. No. 5,235,606 with some variations as described below. Other laser means include glass, LiSAF, dyes, LiCAF, and the like.

The illustrative examples described below generally pertain to laser pulse energies in the 1 joule (J) to 5 joule (J) range with pulse width in the range of 100 fs (femtoseconds) to 1 ps (picoseconds) and the wave length on the order of 1 micron (μm). But these examples are merely illustrative and the invention is not limited thereby.

Figure 5:
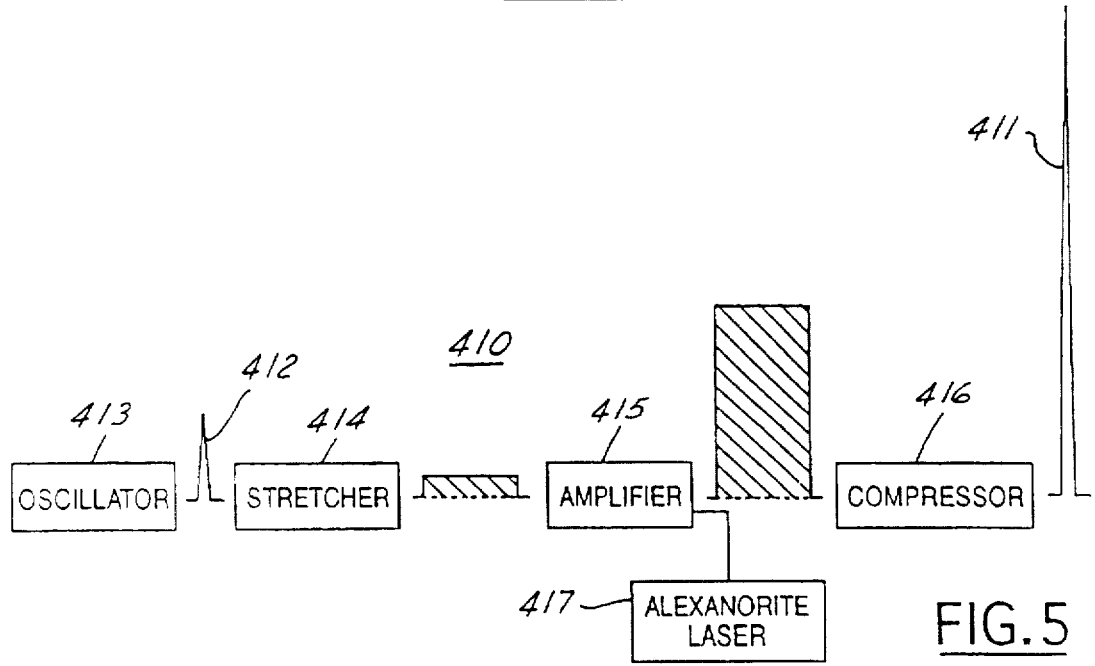
FIG. 5 is a schematic representation of a chirped pulse amplification (CPA) arrangement.

In a basic scheme for CPA laser (410) of FIG. 5, an ultrahigh peak power pulse (411) is produced. First a short pulse (412) is generated. Ideally the pulse (412) from the oscillator (413) is sufficiently short so that further pulse compression is not necessary. After the pulse is produced it is stretched in a stretcher (414) comprising mirrors and gratings arranged to provide positive group velocity dispersion. The amount the pulse is stretched depends on the amount of amplification. A first stage of amplification typically takes place in either a regenerative or a multipass amplifier (415) which is pumped by laser (417). In one configuration this consists of an optical resonator that contains the gain media, a Pockels cell, and a thin film polarizer. After the regenerative amplification stage the pulse can either be recompressed or further amplified. The compressor (416) consists of a grating or grating pair arranged to provide negative group velocity dispersion. Gratings used in the compressor are designed, constructed, and arranged to cooperate with those in the stretching stage. More particulars of a typical system are described in U.S. Pat. No. 5,235,606, previously incorporated herein by reference.

System Modeling

As can be seen, the Laser-Injector Laser ACcelerator (LILAC) of the invention is a stand-alone, desktop-scale, and cost effective electron accelerator which uses two ultrashort and ultraintense laser pulses; the first pulse to generate the highly acceleration efficient electron plasma wave (EPW) and the second one to accelerate a portion of the background electrons (in the PW) supporting the EPW. While not wishing to hold to any particular theory, the model which describes the physics of the LILAC is thought to be as follows. The LILAC mainly consists of three different stages of the acceleration process. The first one is the formation of acceleration medium (plasma wave) by a pump pulse by Laser Wakefield Accelerator (LWFA) to generate EPW in a z direction. The pertinent variables are listed below:

$a_0^2$: normalized pump laser pulse intensity

Φ: EPW amplitude

ω: laser frequency $ω_p$: EPW frequency

Figure 6:
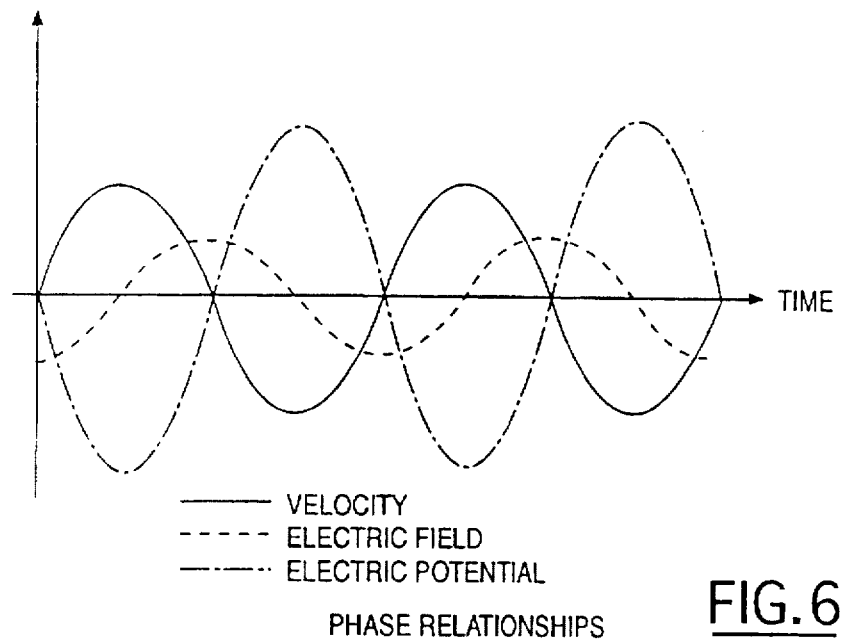
FIG. 6 is a schematic showing the phase relationships among electron velocity, plasma wave electric field, and plasma wave field electric potential.
Figure 7:
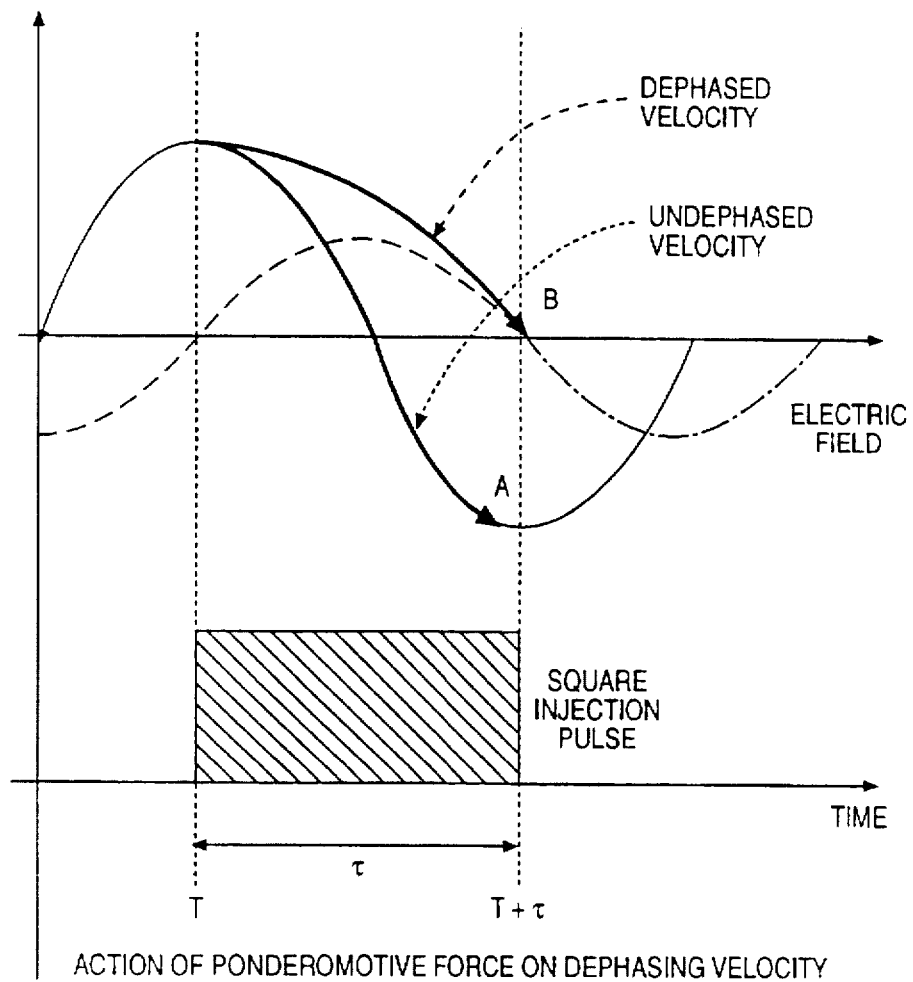
FIG. 7 is a schematic showing the action of ponderomotive force of the injection beam causing the dephasing electron velocity, curve B, compared to undephased velocity, curve A.

Then, $Φ=f(a_0^2)$. This EPW follows a phase relationship as shown in FIG. 6, between potential, fluid velocity, and electric field, so that background electrons can't be accelerated by their own plasma electric field, except when the plasma wave is very large. Note that velocity and electron potential are out-of-phase in FIG. 6. The second laser pulse (injection pulse) is injected into EPW perpendicular (orthogonal) to the direction of $a_0$ (y direction for convenience). The pertinent variables are listed below:

$b_0^2$: normalized injection laser pulse intensity $r_0$: spot size of the injection pulse $Z_i$: position of the center of laser pulse in z axis The ponderomotive force of $b_0$ in z direction dephases the velocities of a group of the EPW background electrons. This concept is shown in FIG. 7 where the electrons are dephased with respect to the plasma wave are illustrated (Curve B). Such electrons dephased with respect to the plasma wave come under the influence of the electric field. As a result of the electron velocity dephasing, EPW electric field, now in-phase with the dephased velocities, accelerates those electrons above the injection threshold for trapping. Finally, those electrons catch up with the plasma wave and are trapped. Electrons in-phase (undephased) are shown in curve A, for comparison.

Figure 8:
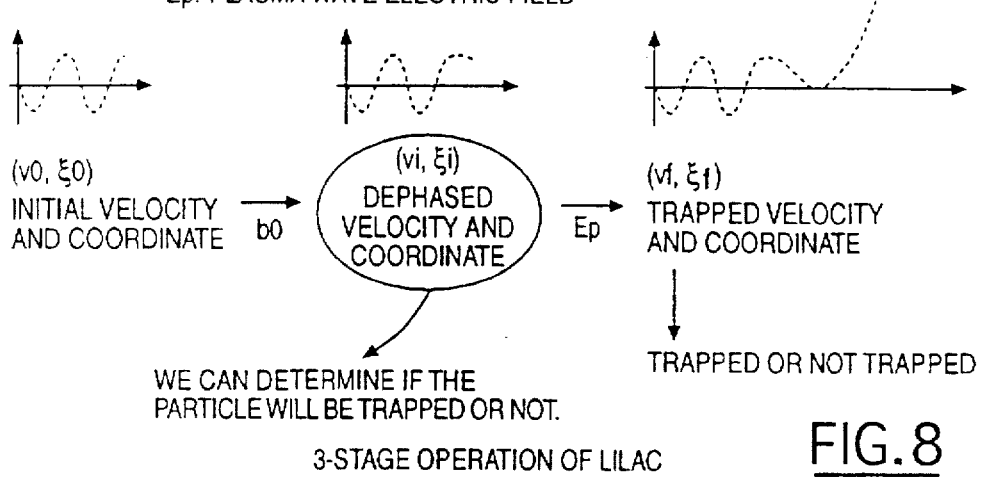
FIG. 8 is a schematic representation of the three stage operation of the LILAC of the invention.

The LILAC mainly consists of three different stages of the acceleration process. This concept is shown in FIG. 8. The non-relativistic ponderomotive force is defined beginning with Equation 3.1 of Table I, where e is electric charge, μ is normalized velocity, ω is laser frequency, E is electric field of laser, χ0 is a positioning coordinate (axis), and $m_0$ is rest mass of electron. The relativistic ponderomotive force is given by Equation 3.2 of Table I, and the μ, normalized velocity, is given in Equation 3.3 of Table I, and alternatively, $λ^2$ is expressed in Equation 3.4 of Table I. In Equation 3.4, the laser wavelength, λ, is in micron and the laser intensity, I, is expressed in W/cm$^2$. It thus follows that $μ^2 ≈ 0.4$ for $I=10^{18}$ W/cm$^2$ and $λ=1$ μm (micron). The relativistic corrective effect of ponderomotive force is to reduce the force down to 20 percent lower than the non relativistic version. To compute $ΔE^2$ first normalized E as per Equation 3.5 and 3.6 of Table I where A is the vector potential. Assume a is the functional form of light pulse as in Equation 3.7 and the square wave envelope and the oscillating portion are given in Equations 3.8 and 3.9, with i being an imaginary number. For relativistic pulse shape in time, replace SQ(t;T, τ) by GS(t;T,τ) which is defined as the Gaussian profile in Equation 3.10. Since ponderomotive force is a time averaged effect, the OSC(t;ω) will drop out of the expression for $F_p$ and the resulting ponderomotive force from the above set of equations is F=F(μ)=F(μ(a)); as per Equation 3.11. The maximum ponderomotive force occurs at $Z-Z_i$ as per Equation 3.12, causing Equation 3.11 to reduce to Equation 3.13. The momentum increase of the background electrons with mass $m_0$ can be written as in Equations 3.14–3.16 with the variables as defined below:

$γ_0$: the relativistic factor of background electrons

T: the time or arrival of the injection pulse

τ: the pulse width of the injection pulse

Thus, T is the time when the ponderomotive interaction between injection pulse and electron begins and T+τ the time when it ends.

Figure 10:
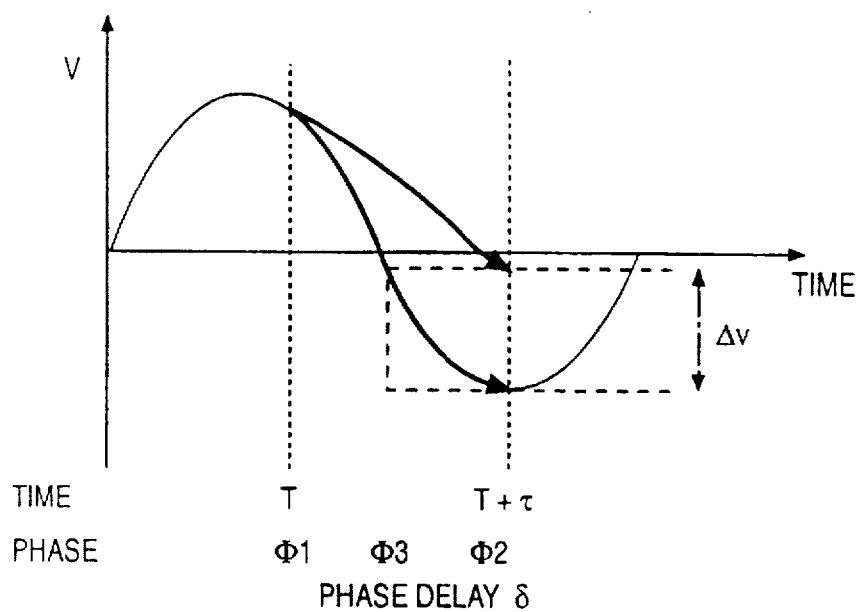
FIG. 10 is a schematic showing phase delay $\delta$.

As to velocity phase drag, define the phase $Φ=ω_p t$, then the proportionality is expressed as per Equation 3.17, where the phase of v is chosen as per Equation 3.18. Now v describes the velocity of the background electrons where $v_m$ is the maximum velocity that background electrons attain during the excursion. Denoting phases $Φ_1$, $Φ_2$ as per Equations 3.19 and 3.20, it is determined that without injection, velocity evolves from T to T+τ according to Φ only. There is no phase drag for velocity as per Equation 3.21. In contrast, with injection, an additional term, ponderomotive force, is introduced thus producing phase drag for velocity as per Equation 3.22. With injection, the background electrons which have interacted with the injection pulse will have a phase drag of velocity oscillation compared to others which have not. The amount of this phase delay can be computed as per Equations 3.23–3.28, where $\Phi_3$ is the phase value of unperturbed $v(\Phi)$ which gives the same velocity perturbed at $t=T+\tau$, and Equation 3.23 can be rewritten as Equation 3.24; which is equivalent to Equation 3.25, and yields Equation 3.26. As can be seen in FIG. 10, the phase delay, $\delta$ is as per Equation 3.27, and $\delta$ is calculated by Equation 3.28.

Figure 9:
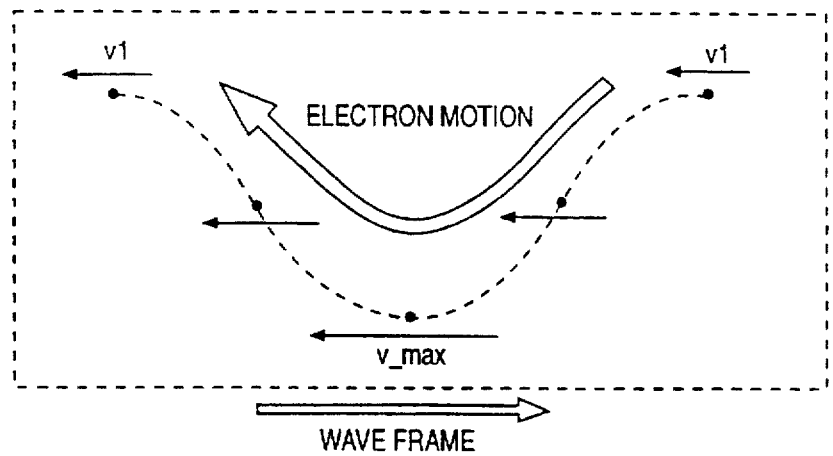
FIGS. 9a and 9b, are schematic representations showing motion of an undephased electron (9a); and motion of a dephased electron (9b) in the plasma wave frame of reference.
Figure 9:
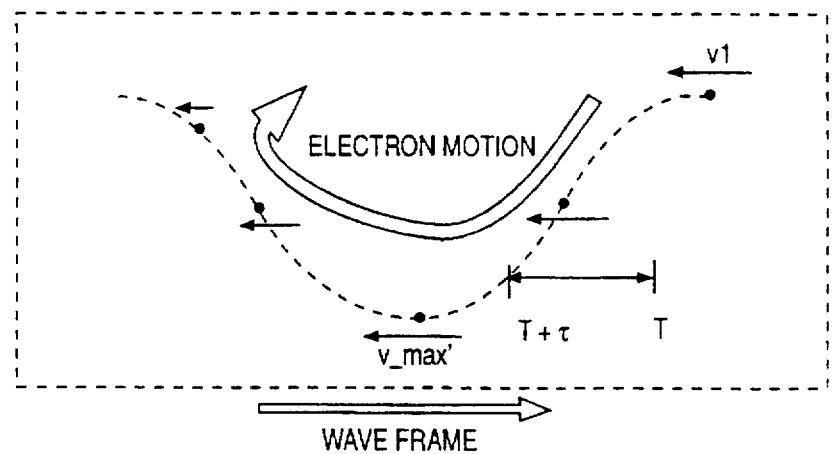

To analyze the trapping threshold, the LILAC is reviewed in moving frame of EPW. In FIG. 9, the velocity dephasing method is described by comparing the motion of an unperturbed background electron and a laser injected electron in the moving frame of reference. It can be understood that the ponderomotive force accelerates the electron while it is on its way down to the valley of the potential. The most general trapping condition is in the moving frame of EPW as per Equation 4.29 with variables as defined below:

$\phi'$: electric potential of EPW $\gamma'$: relativistic factor of the background electron The quantities have Lorentz and inverse Lorentz transformation property as per Equations 4.30–4.32. Thus, given the $\phi'$ at the time T+$\tau$, one can compute the minimum value of injection kinetic energy of the particle, $(\Gamma-1) m_0c^2$ where $\Gamma$ is defined as per Equation 4.33 and where $\epsilon$ is defined as per Equation 4.34. The formation of LILAC depends on whether a background electron is dephased in velocity so that the $\delta$ exceeds the $\Gamma$ in Equation 4.33. The phase delay in velocity $\delta$ is the most relevant quantity for determining the trapping of that particular electron since the plasma wave potential and electric field is not severely modified by the injection pulse. In FIG. 10, the concept of the phase delay in velocity is introduced graphically. Since $\Phi=\omega_p t$, one derives Equation 4.35. The relativistic factor $\gamma'$, which is a function of the velocity of the electron which has already been dephased by $\delta$, should also have a phase delay of $\delta$ as per Equation 4.36. Following the definition of the trapping condition, one concludes that a background electron will be trapped if $\phi'_{inj}$, $\gamma'_{inj}$, and $e\phi'_{inj}$ meet criteria as per Equations 4.37 to 4.39. Assuming $v=v_m\Im(e^{i\Phi})$, the phase relationships yield a phase convention for $\phi$, as per Equation 4.40, and Equation 4.37 is equivalent to saying that in the lab frame $\phi_{inj}$ is equal to the values given in Equations 4.41 to 4.43. Equation 4.38 is equivalent to saying that in the lab frame $\gamma_{inj}$ is as per Equations 4.44 and 4.45, where $v(\Phi_3)$ is derived as per Equations 4.46 and 4.47. Since $\delta$ is a function of T, $\tau$ and $b_0^2$ defined in Equation 3.28 then, Equation 4.39 determines $\Gamma$, $\epsilon_{inj}$, and $\gamma_{inj}$ as per Equations 4.48 to 4.50. In order to solve Equations 4.43, 4.45, 4.47, 4.48, 4.50, and 4.51 for injection threshold vale of $b_0$, rewrite Equation 4.45 as per Equation 4.52. Then, plug Equation 4.52 into Equation 4.51 to get Equation 4.53 and solve Equation 4.53 for $F_p$, ponderomotive force, as per Equation 4.54 and assuming $F_p \approx (F_p)_{max}$ in Equation 3.13, rewrite Equation 4.54 as per Equation 4.55. To express $v_m$ in terms of $\epsilon_{max}$, note that by 1-D nonlinear fluid theory, the velocity of the background electrons in EPW has the following relationship with the normalized electric potential $$E = \frac{e\phi}{m_0c^2}.$$

It is thus possible to use Equations 4.56 and 4.57 and rearrange Equation 4.55 to give the expression for the injection threshold of $b_0$ given $r_0$, T, $\tau$, and all the other parameters as per Equation 4.58. Equations 4.33 and 4.58 are referenced in a paper by T. Katsoulears et al., UCLA, PPG-854 (1985) Equation 4.58 together with Equations 4.48 and 4.50 determines the approximate value of $b_0$ for LILAC operation.

TABLE I

| | |
|---|---|
| $\vec{F}_p = -\frac{e^2}{4m\omega^2} \nabla E^2(\vec{x})$ | (3.1) |
| $\vec{F}_p = \begin{cases} \frac{1}{\sqrt{1+\mu^2}} \frac{m_0c^2}{2} \nabla \mu^2, & \text{(circular polarization)} \\ \frac{1}{\sqrt{1+\mu^2}} \frac{m_0c^2}{4} \nabla \mu^2, & \text{(linear polarization)} \end{cases}$ | (3.2) |
| $\mu^2 = \frac{e^2 \vec{E}^2}{m_0^2 c^2 \omega^2}$ | (3.3) |
| $\mu^2 = \frac{r_0 \lambda^2 I}{\pi m_0 c^3} = 4 \times 10^{-19} \lambda^2 I$ | (3.4) |
| $\vec{A} = \frac{m_0c}{e} \vec{a}$ | (3.5) |
| $\vec{E} = -\frac{\partial \vec{A}}{\partial t} = \frac{-m_0c}{e} \omega \vec{a}$ | (3.6) |
| $\vec{a} = b_0 \times \exp\left[-\left(\frac{z-z_i}{r_0}\right)^2\right] \times SQ(t, T, \tau) \times OSC(t, \omega)$ | (3.7) |
| $SQ(t, T, \tau) = \begin{cases} 1, & \text{if } t < T+\tau, \text{ and } t > T \\ 0, & \text{otherwise} \end{cases}$ | (3.8) |
| $OSC(t, \omega) = e^{i\omega t}$ | (3.9) |
| $GS(t, T, \tau) = \exp\left[-\left(\frac{t-T-\tau/2}{\tau/2}\right)^2\right]$ | (3.10) |
| $F_p(z, t) = b_0^2 \frac{m_0c^2}{\sqrt{1+\mu^2}} \left(\frac{z-z_i}{r_0}\right) \times$ | (3.11) |
| $\exp\left[-2\left(\frac{z-z_i}{r_0^2}\right)^2\right] \times \begin{cases} SQ(t) \\ GS(t) \end{cases}$ | |
| $z - z_i = r_0/2$ | (3.12) |
| $(F_p)_{max} = b_0^2 \frac{m_0c^2}{r_0} \frac{\exp(-1/2)}{2\sqrt{1+\mu^2}}$ | (3.13) |
| $\Delta p = \gamma_0 m_0 \Delta v$ | (3.14) |
| $= \int_T^{T+\tau} F_p(t) dt$ | (3.15) |
| $= F_p \tau \text{(for Super-wide pulse)}$ | (3.16) |
| $v, \phi, E \propto e^{i\Phi}$ | (3.17) |
| $v = \Im(v_m e^{i\Phi})$ | (3.18) |
| $\Phi_1 = \omega_p T$ | (3.19) |

TABLE I-continued $$\Phi_2 = \omega_p(T + \tau) \tag{3.20}$$

$$\upsilon(\Phi_1) \to \upsilon(\Phi_2) \tag{3.21}$$

$$\upsilon(\Phi_1) \to \upsilon(\Phi_2) + \Delta\upsilon \tag{3.22}$$

$$\upsilon(\Phi_2) + \Delta\upsilon = \upsilon(\Phi_3) \tag{3.23}$$

$$\Im(\upsilon_m e^{\Phi_2}) + \Delta\upsilon = \Im(\upsilon_m e^{\Phi_3}) \tag{3.24}$$

$$\upsilon_m \sin\Phi_2 + \Delta\upsilon = \upsilon_m \sin\Phi_3 \tag{3.25}$$

$$\Phi_3 = \sin^{-1}\left( \sin\Phi_2 + \frac{\Delta\upsilon}{\upsilon_m} \right) \tag{3.26}$$

$$\delta = \Phi_2 - \Phi_3 \tag{3.27}$$

$$\delta = \Phi_2 - \Phi_3 = \Phi_2 - \sin^{-1}\left( \sin\Phi_2 + \frac{\Delta\upsilon}{\upsilon_m} \right) \tag{3.28}$$

$$e\phi' \geq (\gamma' - 1)m_0 c^2 \tag{4.29}$$

$$\phi' = \gamma_\phi \phi \tag{4.30}$$

$$\gamma' = \gamma_\phi \gamma(1 - \beta_\phi \beta) \tag{4.31}$$

$$\gamma = \gamma_\phi \gamma'(1 + \beta_\phi \beta') \tag{4.32}$$

$$\Gamma - 1 = \gamma_\phi^2 \{ \epsilon + 1/\gamma_\phi - \beta_\phi (\epsilon + 2/\gamma_\phi) \epsilon |^{1/2} \} - 1 \tag{4.33}$$

$$\epsilon = \frac{e\phi}{m_0 c^2} \tag{4.34}$$

$$\phi'(T + \tau) = \phi'(\Phi_2) \tag{4.35}$$

$$\gamma'(T + \tau) = \gamma'(\Phi_2 - \delta) = \gamma'(\Phi_3) \tag{4.36}$$

$$\phi'_{inj} = \phi'_{max} - \phi'(\Phi_2) \tag{4.37}$$

$$\gamma_{inj} = \gamma'(\Phi_3) \tag{4.38}$$

$$e\phi'_{inj} \geq (\gamma_{inj} - 1)m_0 c^2 \tag{4.39}$$

$$\phi = \phi_{max} \Im(e^{i\Phi + i\pi}) = -\phi_{max} \sin\Phi \tag{4.40}$$

$$\phi_{inj} = \phi_{max} - \phi(\Phi_2) \tag{4.41}$$

$$= \phi_{max}(1 + \sin\Phi_2) \tag{4.42}$$

$$= \phi_{max}(1 + \sin\omega_p(T + \tau)) \tag{4.43}$$

$$\gamma_{inj} = \gamma'(\Phi_3) \tag{4.44}$$

$$= \frac{1}{\sqrt{1 - \frac{\upsilon(\Phi_3)^2}{c^2}}} \tag{4.45}$$

$$\upsilon(\Phi_3) = \upsilon(\Phi_2 - \delta) = \upsilon(\omega_p(T + \tau) - \delta) \tag{4.46}$$

$$= \upsilon_m \sin\omega_p(T + \tau) + \frac{F_p \tau}{\gamma_0 m_0} \tag{4.47}$$

$$\Gamma = \gamma_\phi^2 \{ \epsilon_{inj} + 1/\gamma_\phi - \beta_\phi (\epsilon_{inj} + 2/\gamma_\phi) \epsilon_{inj} |^{1/2} \} \tag{4.48}$$

$$\epsilon_{inj} = \frac{e\phi_{inj}}{m_0 c^2} \tag{4.49}$$

$$= \frac{e\phi_{max}(1 + \sin\omega_p(T + \tau))}{m_0 c^2} \tag{4.50}$$

$$\gamma_{inj} \geq \Gamma \tag{4.51}$$

$$\gamma_{inj} = \frac{1}{\sqrt{1 - \frac{1}{c^2}\left( \upsilon_m \sin\omega_p(T + \tau) + \frac{F_p}{\gamma_0 m_0} \tau \right)^2}} \tag{4.52}$$

$$1 - \frac{1}{c^2}\left( \upsilon_m \sin\omega_p(T + \tau) + \frac{F_p}{\gamma_0 m_0} \tau \right)^2 \leq \frac{1}{\Gamma^2} \tag{4.53}$$

$$F_p \geq \frac{\gamma_0 m_0}{\tau}\left( c\sqrt{1 - \frac{1}{\Gamma^2}} - \upsilon_m \sin\omega_p(T + \tau) \right) \tag{4.54}$$

$$b_0^2 \frac{m_0 c^2}{r_0} \frac{\exp(-1/2)}{2\sqrt{1 + \mu^2}} \tag{4.55}$$

$$\geq \frac{\gamma_0 m_0}{\tau}\left( c\sqrt{1 - \frac{1}{\Gamma^2}} - \upsilon_m \sin\omega_p(T + \tau) \right)$$

$$\beta = \frac{1 - (1 + \epsilon)^2}{1 + (1 + \epsilon)^2} \tag{4.56}$$

$$\upsilon_m = c\left| \frac{1 - (1 + \epsilon_{max})^2}{1 + (1 + \epsilon_{max})^2} \right| \tag{4.57}$$

$$b_0^2 \geq 2\frac{r_0}{c\tau} \frac{\gamma_0 \sqrt{1 + \mu^2}}{\exp(-1/2)}\left( \sqrt{1 - \frac{1}{\Gamma^2}} - \left| \frac{1 - (1 + \epsilon_{max})^2}{1 + (1 + \epsilon_{max})^2} \right| \sin\omega_p(T + \tau) \right) \tag{4.58}$$

In order to test the model of the method, a simulation of single particle in two dimension was performed. The relativistic equation of motion was solved to follow the trajectory of a trapped electron in the phase space. The codes validity was tested using the ponderomotive force of the injection pulse and the trapping of an electron in the plasma wave, to see if they are consistent with the motion expected.

Figure 11:
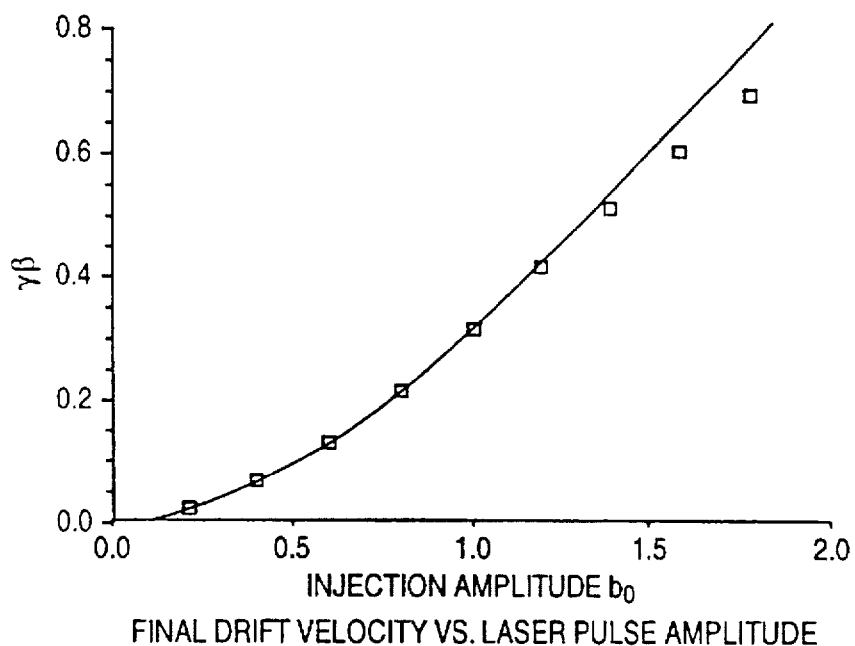
FIG. 11 is a plot showing electron final drift velocity along the direction perpendicular to the propagation of the injection pulse as a function of the injection amplitude.

In FIG. 11, the final drift velocity along the direction perpendicular to the propagation of the injection pulse is shown as a function of the injection pulse amplitude. Gaussian shape for injection pulse spotsize and width is chosen. The electron starts at rest at t=0, a distance $r_0/2$ away from the center of the injection pulse. It is accelerated to the final drift velocity as the pulse passes by. $r_0/2$ was chosen since that is where the ponderomotive force is maximum. ($\pi$ is pi and e is natural number, log scale.) Thus, the curve represents:

$$(\gamma\beta)_{drift} = \frac{b_0^2}{\sqrt{1 + b_0^2/2}} \sqrt{\pi/8} e^{-1/2} ,$$

The points plotted out in the figure represents the simulations and the agreement is well established except at high values of $b_0$. The deviation has come from the fact that the amplitude of the ponderomotive force in the curve is always calculated at the $z=r_0/2$. With a high value of $b_0$, the z displacement of the particle is prominent and the maximum ponderomotive force assumption holds true no longer.

Figure 12:
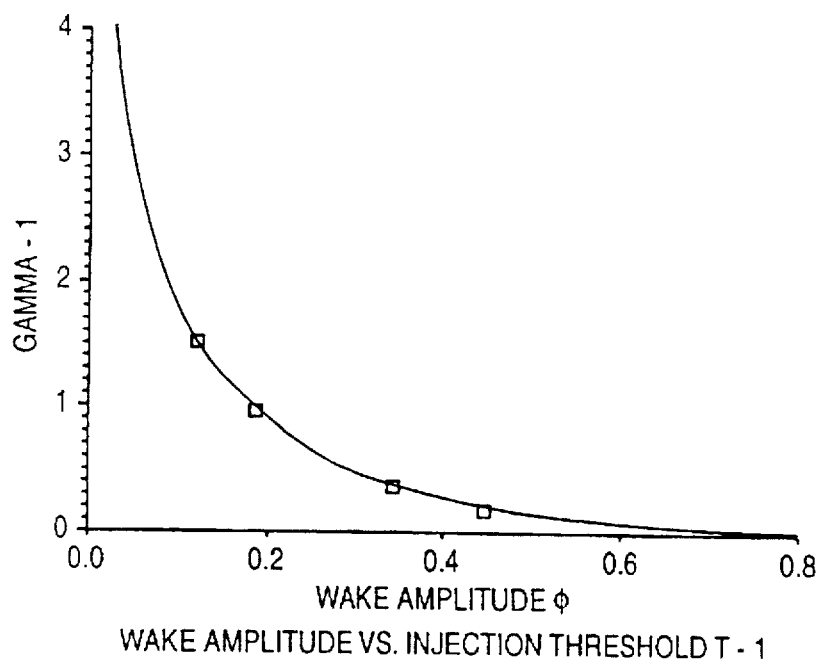
FIG. 12 is a plot of the trapping formula shown as Equation 4.33 in Table I where trapping is simulated for waves of various amplitude.

In FIG. 12, the trapping formula, Equation 4.33 is plotted and using the same simulation trapping is observed for waves of various amplitude. The points represent the fact that the electron with an initial and an initial position at the maximum of electric potential would be trapped.

Figure 13:
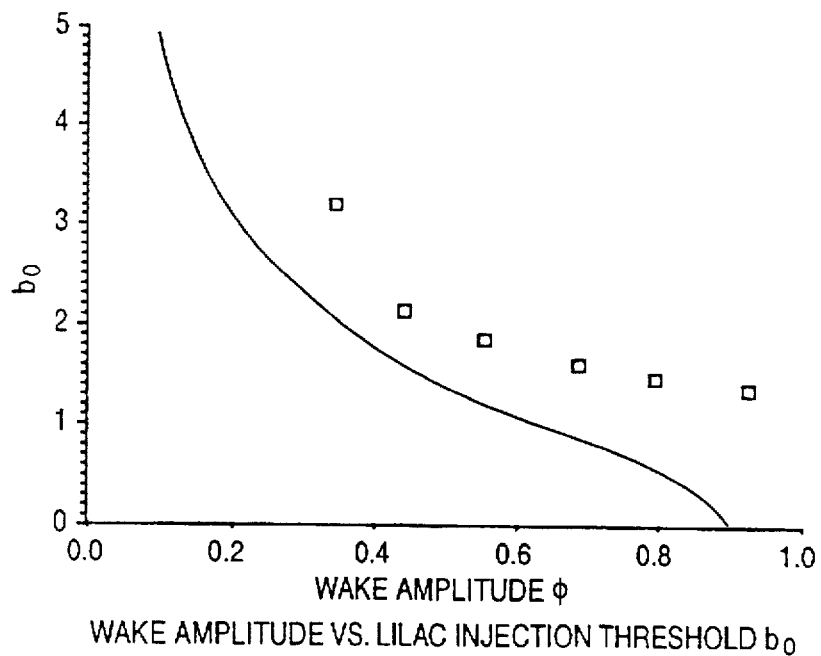
FIG. 13 is a plot where the solid line represents the curve that is obtained from coupling the trapping and drift velocity formulas directly; the dotted line is the numerical solution of the model; and the rectangular points are obtained from the simulation of wakefield amplitude versus injection threshold.

Observing that the code produced the agreeable results on the tests for ponderomotive force and trapping, it is possible to link the two curves since the final drift velocity that can be obtained from the ponderomotive force is used to inject electrons into the plasma wave. In FIG. 13, the drift and the injection velocity are coupled so that the energy coming from the ponderomotive drift gives a trapping threshold curve in terms of $b_0$. The solid line represents the curve that can be obtained from coupling the trapping and the drifting velocity formula directly. The explicit form of this curve is:

$$b_0 = \sqrt{\chi^2/4 + \sqrt{\chi^4/16 + \chi^2}} ,$$

where $$\chi = \sqrt{8/\pi e^{1/2}} \sqrt{\Gamma^2 - 1}$$

The dotted line is the numerical solution of the same model. The discrepancy occurs between the above expression and the numerical solution because of approximations needed to solve for an analytic expression of the drift velocity. The rectangular points are from the simulation. They show the same tendency of the other two curves, though they do not agree with the ponderomotive drift model. The physical interpretation of this is simple, the larger the plasma wave amplitude becomes, the easier it is to trap the electron. There is still some disagreement between the predicted and the simulated results. This is because there were several approximations in order to make the FIG. 13. The plot was made as if the electron is pre-accelerated only by the ponderomotive force of injection pulse without the influence of the plasma wave. In reality, the electrons will be accelerated within the plasma wave electric field and the phase of the injected electrons with respect to the plasma wave will account for the discrepancy between the simulation points and the predicted curve in FIG. 13.

It was determined that it is necessary to match the velocity of the electron to the phase velocity of the wave for the electron to gain energy from the plasma wave. The phase velocity of the plasma wave is about the speed of light, almost C. An electron at C has energy of about an MeV. Therefore, it is necessary to impart to the electron a change in momentum such that it will end up with that final velocity while it is still in the region where it comes under the influence of the electric field for acceleration by the plasma wave. The intensity necessary to do this corresponds to a gain in energy equal to the rest mass of the electron which is about an MeV, and the energy required is approximately $10^{18}$ W/cm² (watts per square centimeter) for 1 µm (micron).

As an example of the principle, a simulation of one possible configuration was performed. The simulation used is of a type known as Particle-in-Cell or PIC. This type of numerical simulation is common in plasma physics, especially in situations where analytic solutions are impossible. Particles representing free electrons and atomic ions move within the confines of a spatial grid under the influence of electric and magnetic fields. The particular PIC code used has one spatial dimension, z, and velocities in three dimensions, x, y, and z. The motion of the particles is calculated using fully relativistic equations of motion for a charged particle in electromagnetic fields. The fields are solved self-consistently for the initial condition and then evolve temporally according to Maxwell's equations.

The chosen characteristics for the simulation are that of a three pulse configuration. There are two pump pulses and a single injection pulse. The first pump drives up the wave while the second identical pump follows the first at a distance of 3/2 the wavelength of the wake in order to drive the wave back down. This creates only a small region for trapping so that the electron beam is very short. The two pump pulses have a laser wavelength of 1 µm (micron) and a length equal to the wavelength of the wake, 10 µm (microns), or 33 femtoseconds. Their normalized intensity is $a_0 = 1.00$. The pump pulse has a length equal to 3 times the length of one of the pump pulses, and its intensity twice that of the pumps, $b_0 = 2a_0 = 2.00$. The spotsize of the injection pulse is $r_0 = 5$ µm (microns), and the position is such that the peak of the injection pulse crosses the axis of the pump pulses one plasma wavelength behind the peak of the first pulse.

Figure 14:
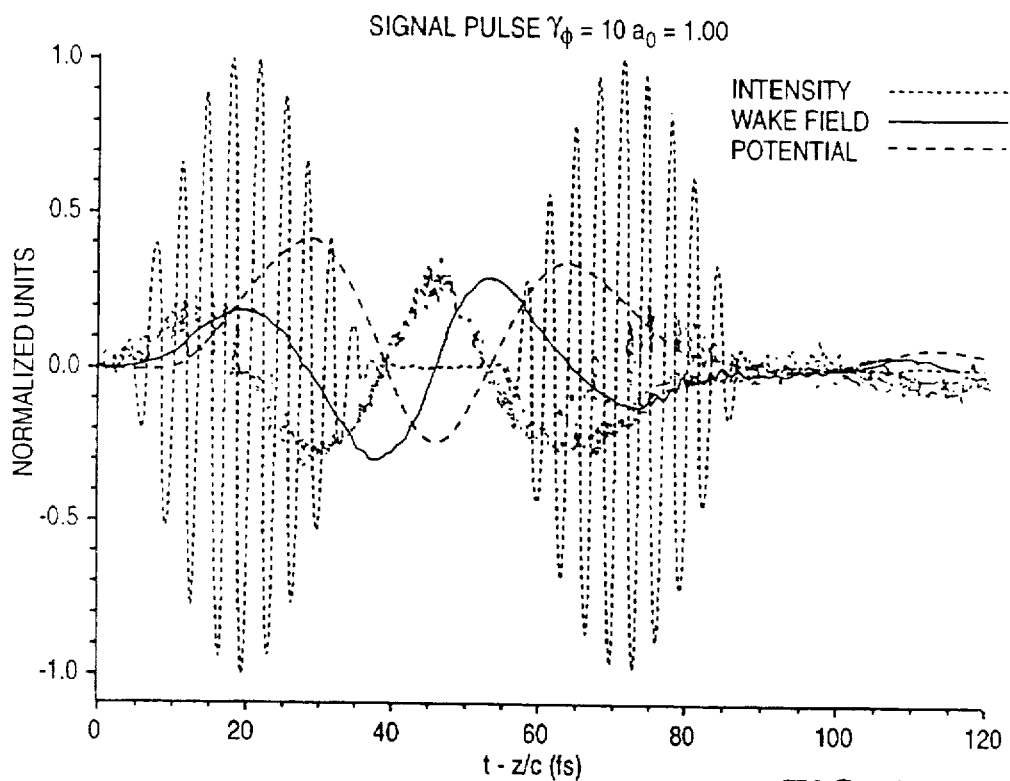
FIG. 14 is a plot of the simulation showing the wave propagating through the plasma in the frame of the moving wave. The four points plotted are: laser intensity is given as small dots; electric field of the wake is given as a solid line; electric potential is given as a dashed line; and individual particle velocities are given as large black dots. The first three quantities are noted on the legend of the plot. The velocities are plotted as individual points on the plot.
Figure 15:
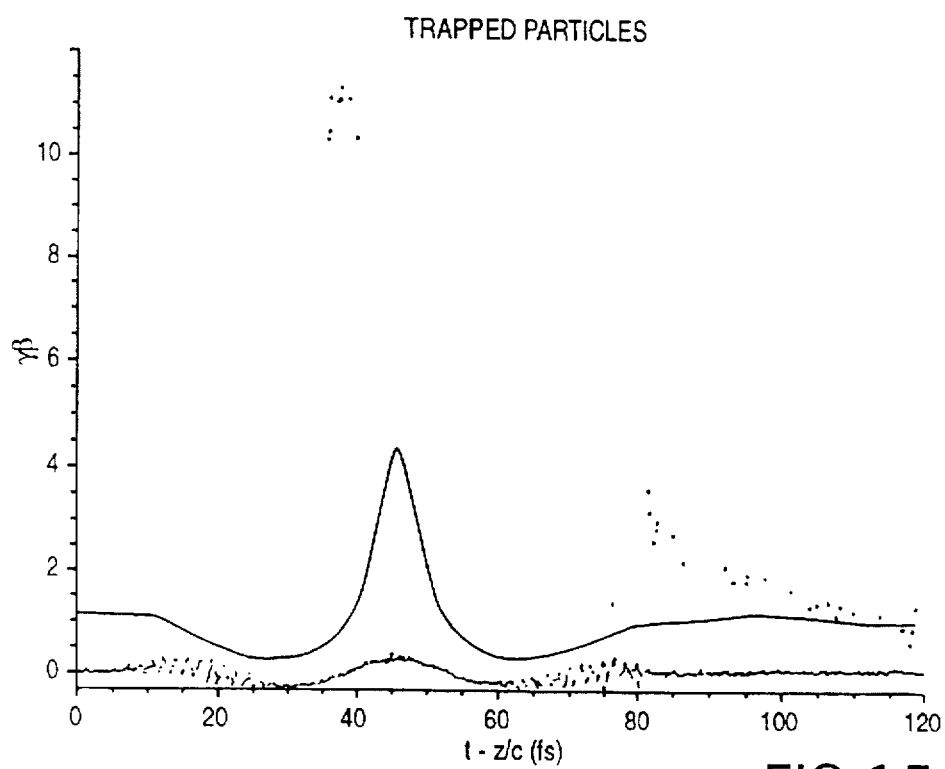
FIG. 15 is a plot of time normalized momenta of the particles, $\gamma\beta$. The solid line represents the trapping condition of Equation 4.33, any particle with a momentum above this line is trapped. At 37 fs (femtoseconds) particles can be seen well above the trapping condition.
Figure 16:
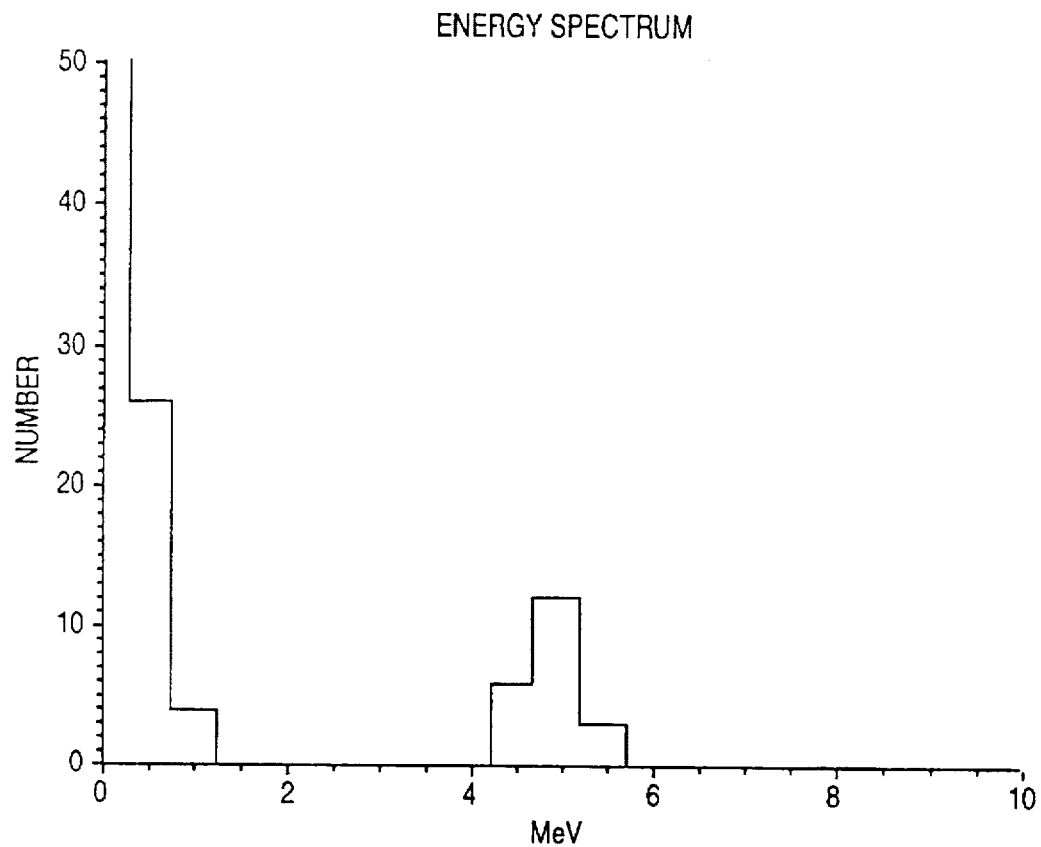
FIG. 16 is a plot showing the energy spectrum of the electrons at the end of the simulation. There are two groups represented. The first is the background electrons with energies of 0 to 1 MeV and the second group is centered at 5 MeV and are the electrons in the beam.

The results of the simulation are summarized in three plots. The first, FIG. 14, is a plot of the wave propagating through the plasma, in the frame of the moving wave. The four quantities plotted are: the laser intensity, $a_0$; the electric field of the wake, $$\frac{eE}{m_0 c \omega_p} ;$$

the electric potential, $$\frac{e\phi}{m_0 c^2} ;$$

and the individual particle velocities, $\beta_z$. The first three qualities are noted on the plot's legend. The velocities are plotted as individual points on the plot. It is clear that after the second pump pulse there is no wake. The particles trapped in the wave forming the beam are centered around 37 fs (femtoseconds). The amplitude of the wave matches the expectation from theory explaining the formation of wakes. FIG. 15 demonstrates the trapping of the particles in the wave. This time normalized momenta of the particles, $\gamma\beta$, are plotted. The solid line represents the trapping condition of Equation 4.33, based on the electric potential of the wave. Any particle with a momentum above this line is then trapped in the wave. Again, at about 37 fs (femtoseconds) the trapped particles can be seen, well above the trapping condition. The phase velocity of the wave is $\gamma\beta = 10$, so the particles are actually moving faster than the wave at this point. The third plot, FIG. 16, shows the energy spectrum of the electrons at the end of the simulation. They fall into two groups, the first is the background electrons with energies ranging from 0 to 1 MeV. The second group centered at 5 MeV, are the electrons in the beam. The plot shows a distinct separation of the beam from the background, with a small energy spread in the injected beam, about 10 percent.

While this particular simulation may not be optimized for the best possible configuration, it does show one possible configuration. It also demonstrates the robustness of this technique, that a beam of excellent quality, small energy spread, can be created even under non-optimal conditions; optimal yet to be determined.

The method and apparatus of the invention are unlike other plasma-based accelerators, which are exclusively second-stage high-energy electron accelerators, requiring a trailing bunch of electrons that have been generated and pre-accelerated in a conventional combination electron gun and linear accelerator (linac).

The invention utilizes laser-driven plasma waves as the first-stage low-energy electron gun/linac itself. As such, it forms the basis for a compact (table-top) source of relativistic electrons, that can either be used by itself or as an injector for high-energy accelerators. Electrons are accelerated to relativistic velocities in a distance less than a millimeter as compared with several meters for a comparable conventional linac, resulting in lower beam emittance and a more compact size. It also produces much shorter-duration electron pulses (femtosecond as compared with picosecond). For applications that require an electron bunch synchronized with a laser-light pulse, femtosecond accuracy may be achieved with the invention. In a preferred embodiment, two orthogonally directed laser beams are injected into a plasma: one beam creates a wakefield plasma wave, and the other alters the trajectory of background electrons in such a way that they become trapped in the plasma wave and are then accelerated to relativistic velocities in a distance less than a millimeter. Compared with a conventional electron linac, the LILAC has a much higher field gradient, resulting in lower beam emittance. Since it also can produce much shorter-duration electron pulses, it can be used for the study of ultrafast dynamics on femtosecond timescales. The invention also enables femtosecond-synchronization between the electron bunch and the plasma wave acceleration field, which is required to achieve a low-energy spread for the accelerated electrons. A high-flux low-emittance beam of 20-MeV electrons can be produced with a currently-available table-top high-intensity laser ($I \leq 1 \times 10^{18}$ W/cm$^2$). The principle upon which the LILAC is based can be used to study the growth of, and the trapping of electrons in, laser wakefield plasma waves.

Figure 17:
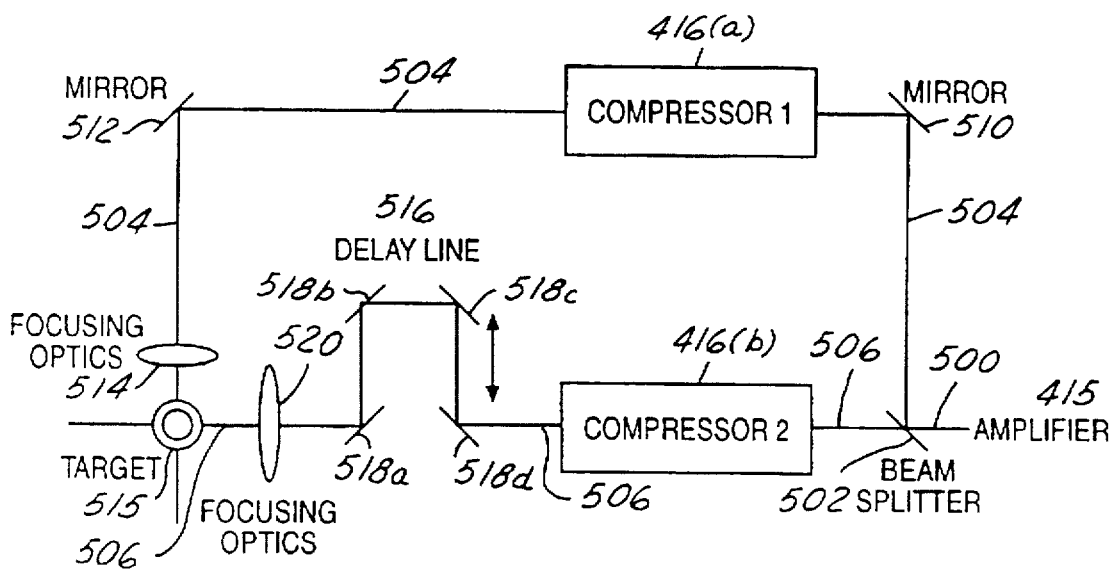

In summary, the pulses of the invention are ultra short pulses generated by laser systems as described in FIGS. 4, 5 and 17. In the method of the invention, the pump pulse and the injection pulse may be obtained from the same laser beam by splitting a single laser pulse into two sub-pulses. The beamsplitting may occur before (FIG. 17) or after (FIG. 4) recompression in the laser system, shown schematically in FIG. 5. If such beamsplitting occurs after recompression (FIG. 4), then the pump and injection pulses are synchronized with respect to one another. The invention may also be used with the beamsplitter (FIG. 17) prior to recompression, in order to achieve pump pulse and injection pulse of different pulse time durations. Therefore, FIG. 17 encompasses the elements of FIGS. 4 and 5, and the beamsplitter 502 is arranged between amplified 415 which was previously shown in FIG. 5, and compressors 416(a) and 416(b), similar to single compressor 416 of FIG. 5. More specifically, in FIG. 17, beam 500 is split by beamsplitter 502 into a first pulse 504 and a second pulse 506. Pulse 504 is directed by mirror 510 to compressor 416(a), then by mirror 512 and optics 514 to target 515. Pulse 506 enters compressor 416(b) and then enters delay line 516, comprising mirrors 518(a), (b), (c), and (d). Next, pulse 506 is directed onto target 515 by optics 520.

While this invention has been described in terms of certain embodiments thereof, it is not intended that it be limited to the above description, but rather only to the extent set forth in the following claims. The embodiments of the invention in which an exclusive property or privilege is claimed are defined in the following claims.

We claim:

1. A method for accelerating electrons comprising: generating a plasma wave in a plasma comprising free electrons and atomic ions, said plasma wave characterized by an electric field; producing dephased electrons that are dephased with respect to said plasma wave; and accelerating said dephased electrons by force of said plasma wave electric field.

2. The method according to claim 1 wherein said dephased electrons are formed by directing a beam comprising at least one laser pulse into said plasma wave to dephase said electrons with respect to said plasma wave.

3. The method according to claim 2 wherein said beam is injected into said plasma wave in a direction different from the direction of propagation of said plasma wave.

4. The method according to claim 2 wherein said laser pulse has an intensity gradient sufficient to alter the trajectory of said free electrons thereby providing said dephased electrons.

5. The method according to claim 2 wherein said dephased electrons are formed from said atomic ions in said plasma by said laser pulse at an intensity sufficient to remove said electrons from said atomic ions thereby providing said dephased electrons.

6. The method according to claim 1 wherein said plasma wave is formed by generating a first beam of at least one pump laser pulse; and directing said pump pulse onto a target to produce said free electrons and atomic ions by photo ionization of said target, and to produce said plasma wave moving in the direction of propagation of said pump pulse.

7. The method according to claim 6 wherein said at least one laser pulse comprises first and second pump laser pulses, said first laser pulse which produces said free electrons and atomic ions, and said second pump laser pulse which produces said plasma wave.

8. The method according to claim 7 wherein said first pulse arrives at said target before said second pulse.

9. The method according to claim 8 wherein said second pulse is delayed with respect to said first pulse for a time sufficient for any plasma wave produced by said first pulse to dampen away.

10. The method according to claim 6 wherein said dephased electrons are produced by generating a second beam of at least one injection laser pulse and directing said injection pulse into said plasma wave, said injection pulse having an intensity sufficient to remove electrons from said atomic ions, thereby providing said dephased electrons.

11. The method according to claim 10 wherein said injection laser pulse has an intensity greater than said pump pulse.

12. The method according to claim 10 wherein said injection laser pulse has an intensity sufficient to remove said electrons from said atomic ions by photo-ionization and to impart to said removed electrons a residual velocity sufficient to cause said electrons to be trapped by said plasma wave.

13. The method according to claim 10 wherein said injection laser pulse removes electrons from said atomic ions at a higher ionization stage than that of said electrons removed by ionization of said target by said pump pulse.

14. The method according to claim 10 wherein said injection laser pulse is collinear with said pump pulse.

15. The method according to claim 10 wherein said injection laser pulse is injected into said plasma wave in a direction orthogonal to the direction of propagation of said pump pulse.

16. The method according to claim 10 wherein said at least one injection laser pulse comprises two injection laser pulses arranged counterpropagating to one another and each directed into said plasma wave at a direction orthogonal to the direction of propagation of said plasma wave to offset any drift of said electrons in a direction transverse to the direction of propagation of said plasma wave.

17. The method according to claim 10 wherein said pump and injection laser pulses are directed into said plasma wave essentially simultaneously.

18. The method according to claim 10 wherein a single pump laser pulse and a single injection laser pulse are used.

19. The method according to claim 10 wherein said injection and pump laser pulses have differing wavelengths.

20. The method according to claim 10 wherein said injection and pump laser pulses have differing pulse widths (pulse time duration).

21. The method according to claim 10 wherein said injection and pump laser pulses have differing polarization.

22. The method according to claim 1 wherein said step of producing said dephased electrons includes altering the position, direction, and velocity of said dephased electrons so as to position said dephased electrons in an optimal region of said plasma wave electric field with a velocity that exceeds the phase velocity of said plasma wave.

23. A method for accelerating electrons comprising the steps of:
 a. generating a beam of at least one pump laser pulse;
 b. directing said pump pulse onto a target to produce a plasma wave in a plasma comprising free electrons and atomic ions; said plasma wave moving in the direction of propagation of said pump pulse, encompassing electrons in-phase with oscillating motion of said plasma wave, and being characterized by an electric field;
 c. generating a beam of at least one injection laser pulse;
 d. directing said injection pulse beam into said plasma wave in a direction transverse to the direction of propagation of said plasma wave to produce dephased electrons that are dephased with respect to the oscillating motion of said plasma wave; and
 e. positioning said dephased electrons in said plasma wave electric field and accelerating said electrons by force of said electric field.

24. The method according to claim 23 wherein said injection laser pulse has an intensity gradient sufficient to alter the trajectory of said in-phase electrons by ponderomotive force thereby providing said dephased electrons.

25. The method according to claim 23 wherein said pump laser pulse and said injection laser pulse have differing wavelengths, pulsewidths, intensities, and/or polarizations.

26. The method according to claim 25 wherein said differing wavelength is achieved by directing one or both of said injection and pump pulses through an optical device which alters the wavelength prior to directing said pulse onto said target.

27. The method according to claim 23 wherein said dephased electrons are produced from electrons present in atomic ions in said plasma and said injection laser pulse has an intensity sufficient to remove said electrons from said atomic ions by photo-ionization thereby providing said dephased electrons.

28. The method according to claim 27 wherein said injection laser pulse has an intensity sufficient to remove said electrons from said atomic ions by photo-ionization and to impart to said removed electrons a residual velocity sufficient to cause said electrons to be trapped by said plasma wave.

29. The method according to claim 23 wherein said at least one injection laser pulse comprises two injection pulses arranged counterpropagating to one another and each directed into said plasma wave at a direction orthogonal to the direction of propagation of said plasma wave.

30. The method according to claim 29 wherein said two injection pulses are injected into said plasma wave essentially simultaneously.

31. The method according to claim 23 wherein a single pump laser pulse and a single injection laser pulse are used.

32. The method according to claim 31 wherein said injection laser pulse is injected into said plasma wave essentially simultaneously with said pump laser pulse or after said pump laser pulse.

33. The method according to claim 23 wherein said injection laser pulse is focused onto said plasma wave by focusing means which provides a beam spot size, which in one dimension substantially corresponds to the radial extent of the plasma wave, and in another dimension corresponds to about one plasma wave wavelength ($\lambda_p$).

34. The method according to claim 23 wherein the plasma wave has an axial extent (z axis) and a radial extent (y axis) and the injection laser pulse is focused onto said plasma wave by focusing means which provides a beam spot size having a dimension along the y axis which is greater than the size along the z axis.

35. The method according to claim 23 wherein first and second pump laser pulses are used, said second pump pulse is generated at an interval of 3/2 plasma wavelengths (3/2 $\lambda_p$) after the first pump pulse, to provide an acceleration region of a single plasma wavelength and thus provide a single electron bunch.

36. The method according to claim 23 wherein the pump pulse beam and the injection pulse beam are each produced from a single laser pulse which is split into two pulses, the first being said pump pulse and the second being said injection pulse.

37. The method according to claim 23 wherein one or both of said pump and injection laser pulses is directed through respective optical means which adjusts the arrival time of said pulses at said target relative to one another.

38. The method according to claim 23 wherein said injection laser pulse arrives at said target during said pump pulse.

39. The method according to any one of claims 2, 6, 10, and 23 wherein each of said laser beams is obtained by chirped pulse amplification means comprising means for generating a laser pulse; means for stretching such laser pulse in time; means for amplifying such time-stretched laser pulse; and means for recompressing such amplified pulse.

40. An apparatus for accelerating electrons comprising:
 a. a vacuum chamber;
 b. laser pulse generating means for generating a beam of one or more laser pulses;
 c. a target supported in said chamber, said target comprising matter which forms a plasma upon bombardment by one or more laser pulses;
 d. beam splitting means which splits each of said generated laser pulses into two sub-pulses, a first sub-pulse and a second sub-pulse;
 e. optical means which delays at least one of said sub-pulses and directs it to said target;
 f. first laser focusing means, disposed between said laser generating means and said target, which focuses said first sub-pulse onto said target and adjusts the size of the spot of the beam and its corresponding intensity incident at said target to produce a plasma wave in said plasma;
 g. second laser focusing means, disposed between said laser generating means and said target, which focuses said second sub-pulse onto said target and adjusts the size of the spot of the beam and its corresponding intensity incident at said target to provide electrons in said plasma which are out of phase with said plasma wave formed by said first sub-pulse; and
 h. said first focusing means and said target arranged in said chamber to define a first path for said first sub-pulse, said second focusing means and said target arranged in said chamber to define a second path for said second sub-pulse which is transverse to the first path.

41. The apparatus according to claim 40 wherein said laser pulse generating means comprises a chirped pulse amplification (CPA) system.

42. The apparatus according to claim 41 wherein said CPA system comprises means for generating an optical pulse, means for stretching the pulse in time, means for amplifying the time stretched pulse including solid state amplifying media, and means for recompressing the amplified pulse.

43. The apparatus of claim 42 wherein said CPA system produces a beam of one or more pulses having an incident intensity of at least about $10^{16}$ watts per square centimeter at a laser pulse time duration of less than a picosecond.

44. The apparatus according to claim 40 wherein said beam splitting means comprises a transparent substrate with a reflective coating that produces partial transmission.

45. The apparatus according to claim 44 wherein said beam splitting means is arranged between said pulse amplifying means and said recompression means, and said recompression means comprises a first compressor which recompresses said pump pulse and a second compressor which recompresses said injection pulse to a pulse time duration different from said pump pulse.

46. The apparatus according to claim 44 further comprising wavelength adjustment means arranged between said beam splitting means and one of said focusing means.

47. The apparatus of claim 40 wherein said second laser focusing means comprises a cylindrical lens or mirror.

48. The apparatus according to claim 44 further comprising a wave plate circular polarizer arranged between said beam splitting means and said second focusing means.

* * * * *